(12) United States Patent
Spriggs

(10) Patent No.: US 10,048,187 B2
(45) Date of Patent: Aug. 14, 2018

(54) IMPROVEMENTS RELATING TO PARTICLE CHARACTERISATION

(71) Applicant: Malvern Instruments Limited, Malvern, Worcestershire (GB)

(72) Inventor: David Spriggs, Malvern (GB)

(73) Assignee: MALVERN PANALYTICAL LIMITED, Malvern, Worcestershi (GB)

( * ) Notice: Subject to any disclaimer, the term of this patent is extended or adjusted under 35 U.S.C. 154(b) by 0 days.

(21) Appl. No.: 15/032,289

(22) PCT Filed: Nov. 4, 2014

(86) PCT No.: PCT/GB2014/053272
§ 371 (c)(1),
(2) Date: Apr. 26, 2016

(87) PCT Pub. No.: WO2015/067930
PCT Pub. Date: May 14, 2015

(65) Prior Publication Data
US 2016/0252443 A1    Sep. 1, 2016

(30) Foreign Application Priority Data

Nov. 5, 2013  (EP) .................................... 13191554
Nov. 5, 2013  (EP) .................................... 13191555
(Continued)

(51) Int. Cl.
*G01N 15/02*  (2006.01)
*G01N 15/14*  (2006.01)
(Continued)

(52) U.S. Cl.
CPC ..... *G01N 15/0205* (2013.01); *G01N 15/0211* (2013.01); *G01N 15/1456* (2013.01);
(Continued)

(58) Field of Classification Search
CPC .......... G01N 15/0205; G01N 15/0211; G01N 15/1456; G01N 15/1459; G01N 21/51;
(Continued)

(56) References Cited

U.S. PATENT DOCUMENTS 5,185,641 A    2/1993  Igushi et al.
5,305,073 A *  4/1994  Ford, Jr. ................. G01N 21/49
                                                    356/338
(Continued)

FOREIGN PATENT DOCUMENTS

EP         0 485 817       5/1992
GB            23491       10/1910
GB       190923491 A  *  10/1910  ............... G02B 3/08

OTHER PUBLICATIONS

"Light Scattering From Bubbles In Water" OCEAN '89, IEEE, vol. 4, Sep. 18, 1989, pp. 1186-1193, XP010222562 by Marston P L.*
(Continued)

*Primary Examiner* — Jamil Ahmed
(74) *Attorney, Agent, or Firm* — Morrison & Foerster LLP

(57) ABSTRACT

A particle characterization apparatus is disclosed comprising: a light source; a sample cell; a collecting lens and a detector. The light source is operable to illuminate a sample comprising dispersed particles within the sample cell with a light beam along a light beam axis. The light beam axis passes through a first wall of the sample cell, through the sample, and through a second wall of the sample cell, so as to produce scattered light by interactions with the sample. The detector is configured to detect light scattered from the sample. The second wall of the sample cell comprises a lens with a convex external surface through which the light beam axis passes. The collecting lens is arranged to collect and
(Continued)

focus scattered light leaving the sample cell onto the detector, and comprises an aspheric surface.

18 Claims, 26 Drawing Sheets

(30) Foreign Application Priority Data

| Nov. 5, 2013 | (EP) | 13191556 |
|---|---|---|
| Nov. 5, 2013 | (EP) | 13191557 |
| Nov. 5, 2013 | (EP) | 13191558 |

(51) Int. Cl.
 *G01N 21/51* (2006.01)
 *G02B 3/02* (2006.01)
 *G01N 21/47* (2006.01)

(52) U.S. Cl.
 CPC ............... *G01N 21/51* (2013.01); *G02B 3/02* (2013.01); *G01N 2021/4707* (2013.01); *G01N 2021/4709* (2013.01); *G01N 2021/4711* (2013.01)

(58) Field of Classification Search
 CPC ........... G01N 21/49; G01N 2021/4707; G01N 2021/4709; G01N 2021/4711; G02B 3/02; G02B 3/08
 See application file for complete search history.

(56) References Cited

U.S. PATENT DOCUMENTS

| 2006/0250604 A1* | 11/2006 | Hamada | G01N 15/1459 |
|---|---|---|---|
| | | | 356/39 |
| 2008/0221711 A1 | 9/2008 | Trainer | |
| 2011/0242535 A1 | 10/2011 | Fröse | |

OTHER PUBLICATIONS

Marston, P. L., (1989), "Light Scattering From Bubbles In Water"; Ocean '89, IEEE, vol. 4, pp. 1186-1193.

International Search Report and Written Opinion, dated Jan. 30, 2015; directed towards PCT Application No. PCT/GB2014/053272; 11 pages.

* cited by examiner

IMPROVEMENTS RELATING TO PARTICLE CHARACTERISATION

CROSS REFERENCE TO RELATED APPLICATIONS

This application is a U.S. National Stage patent application of PCT/GB2014/053272 filed on Nov. 4, 2014, which claims priority to European Patent Application Nos. 13191558 filed on Nov. 5, 2013, Ser. No. 13/191,556 filed on Nov. 5, 2013, Ser. No. 13/191,554 filed on Nov. 5, 2013, Ser. No. 13/191,557 filed on Nov. 5, 2013, and Ser. No. 13/191,555 filed on Nov. 5, 2013, each one of which is hereby incorporated by reference in their entirety.

The present invention relates to an apparatus for characterising particles, and to a method for use in characterising particles. Characterising particles may comprise determining a distribution of particle size.

It is known that particles in a sample can be characterised by illuminating the sample and measuring the light scattered by the particles. The particles of the sample are typically dispersed within a sample cell in a dispersant medium during measuring. The dispersant medium is typically air or water, and typically flows through the sample cell during measurement.

In this type of instrument the sample cell conventionally has a pair of flat, parallel transparent walls, and the sample is illuminated through a first wall. Forward scattered light leaves the sample cell via the opposite second wall, and backscattered light leaves the sample cell via the first wall. This arrangement is suitable for measuring both the relatively low scattering angles associated with large particles and the higher scattering angles associated with small particles.

In a different type of instrument the sample is illuminated with a light beam that is parallel to the walls of the sample cell, and light scattered sideways through the walls of the sample cell is detected. Such instruments are referred to as multi angle light scattering (MALS) instruments, and are typically used for measuring molecular weight and the size of very small particles in a liquid, such as macromolecules. MALS instruments are not suitable for characterising a broad range of particle sizes, in particular for characterising larger particles. US 2011/0242535 discloses a MALS instrument in which a wall of the measurement cell comprises a curved surface. A light absorbing device, such as a light absorbing coating, is preferably installed on the wall opposite to the curved side of the sample cell.

EP 0485817 discloses an apparatus for measuring particle size distribution wherein the sample cell comprises a wall that is parallel to the axis of a light beam illuminating the sample, and a further wall at 45 degrees to the axis of the light beam.

US 2008/0221711 discloses an interferometric arrangement for determining particle characteristics using scattered light, in which a sample cell is inclined at approximately 45 degrees to the illuminating light beam. One consequence of this arrangement is that light scattered at relatively high angles (above the critical angle for a water/air interface) can escape from the sample cell without total internal reflection at the exit interface of the cell. A drawback of inclining the cell in this way is that light scattered at relatively low angles has a high angle of incidence at the interface between the sample and the sample cell, resulting in increased reflections which result in higher optical noise and decreased signal to noise ratio. Prisms at the external surfaces are proposed to reduce reflections at the external interface of the sample cell (by reducing the angle of incidence at this interface).

An arrangement suitable for detecting light scattered at a broad range of scattering angles with a high signal to noise ratio is desired.

The correlation between light scattering and particle characteristics can be described by the well known Mie solution to Maxwell's equations. Smaller particles tend to result in larger scattering angles, and larger particles result in smaller scattering angles. The light scattered at each of a range of angles from the sample can be used to determine, for example, a size distribution of the particles in the sample.

One problem with existing systems for particle characterisation by light scattering is signal to noise ratio. When small amounts of scattered light must be detected in order to characterise the particles, electronic noise or optical noise may make reliable measurements difficult to achieve. Optical noise may arise from a number of sources, including bubbles, detritus on the various optical elements, leaching of chemicals into the sample, dispersant index gradients and errors in background subtraction.

Where the dispersant is water, a further problem tends to arise in prior art particle characterisation systems. The angle of light scattered at an initial scattering angle in water will increase on refraction at the interface between the sample cell and air, which tends to decrease the intensity of scattered light per steradian for detection. Furthermore, light scattered above a critical angle will be totally internally reflected at the interface between the sample cell and air. This reflected light will end up as a weak haze of light that tends to contaminate the scattered light, contributing to optical noise.

It is an object of the invention to overcome or least ameliorate one or more of the above mentioned problems.

According to a first aspect of the invention, there is provided a particle characterisation apparatus comprising: a light source; a sample cell; and a detector; wherein the light source is operable to illuminate a sample comprising dispersed particles within the sample cell with a light beam along a light beam axis, the light beam axis passing through a first wall of the sample cell, through the sample, and through a second wall of the sample cell, so as to produce scattered light by interactions with the sample; wherein the detector is configured to detect scattered light leaving the sample cell; and wherein the first wall and/or second wall of the sample cell comprise a convex external surface through which the light beam axis passes.

The second wall may comprise a lens with a convex external surface through which the light beam axis passes. The detector may be arranged to detect light scattered from the sample at an angle of less than 90 degrees to the light beam axis (forward scattered light).

The apparatus may comprise a collecting lens. The collecting lens may be arranged to collect and focus scattered light leaving the sample cell onto the detector. The detector may comprise a planar detector. The collecting lens may comprise an aspheric surface. The aspheric surface may be configured to reduce field curvature at the planar detector.

As discussed in more detail below, the use of a lensed second wall of the sample cell allows light scattered at high scattering angles to escape. The present applicant has found that trying to capture and detect as much light as possible over a broad range of scattering angles that includes high scattering angles tends to result in designs with larger ranges of scattering angles at the detector, which can result in field curvature at the detector. This problem has not previously been identified.

A strong prejudice against the use of aspheric surfaces is present in the field of scattered light detection. The manufacture of an aspheric surface tends to result in reduced surface quality of the lens, which in turn results in increased light scattering at the aspheric surface. This contributes to optical noise, especially where the light beam passes through the collecting lens. Consequently, spherical surfaces have previously been preferred in collecting lenses, because these result in reduced scattering.

The applicant has found that a collecting lens with an aspheric surface is advantageous in the context of a light scattering instrument having a sample cell having a lensed second wall. For example, the correction of field curvature at the detector provides a substantial benefit of enabling a planar detector to detect light scattered over a broader range of angles without defocusing of the scattered light as a result of field curvature. The applicant has also found that more compact optical arrangements are facilitated using a collection lens comprising an aspheric surface than would be the case using conventional spherical lenses.

There may be more than one collecting lens, and more than one aspheric surface. Each of a plurality of collecting lenses may have an aspheric surface. The apparatus may comprise at least one further collecting lens that does not comprise an aspheric surface.

The collecting lens may be configured such that the light beam does not pass through the aspheric surface. When the illuminating light beam passes through an aspheric surface, the scattering of the light beam results in a considerable increase in noise.

In some embodiments the collecting lens may comprise a face with an aspheric surface spherical surface (having better surface quality than the aspheric surface), with the light beam passing through the spherical surface. Such an arrangement enables the improved performance in collecting and focussing scattered light at a detector, while obviating the increased scattering that would tend to occur when the illuminating light beam passed through the aspheric surface.

A lens with a face comprising an aspheric surface and a spherical surface may be produced by taking a spherical lens, and then re-grinding an aspheric surface in the face, while leaving a high quality spherical surface region intact. Alternatively the starting point may be a moulded aspherical lens, in which a region or surface of the face is ground to have a high surface quality, for instance by grinding a spherical surface. The spherical or high quality surface or region may comprise a central region of the face (i.e. on the axis of the lens).

A deflector element may be positioned to prevent the light beam from reaching the aspheric surface of the collecting lens. For instance, an angled mirror may be positioned on the light beam axis prior to the light beam reaching the collecting lens, to deflect the light beam away from the collecting lens, thereby preventing scattering of the light beam from the aspheric surface. The angle mirror may be small, relative to the collecting lens, being large enough to deflect substantially all of the light beam away from the collecting lens, without being large enough to scattered light away from the collecting lens. The deflector element may comprise a mirror or prism. The deflector element may subtend a scattering angle of less than: 5, 3, 2, 1, or 0.5 degrees.

The collecting lens may comprise an open region through which the light beam passes. The open region of the collecting lens may include the lens axis.

The detector may comprise a planar detector arranged to detect light scattered from the sample at a range of angles, the range of angles comprising a minimum scattering angle of 30 degrees or less, and a maximum scattering angle of 50 degrees or more.

The minimum scattering angle may be selected from: 0.1, 0.5, 1, 2, 5, 10, 15, 20 and 30 degrees. The maximum scattering angle may selected from: 40, 50, 60, 70 and 80 degrees. The use of a single planar detector for detecting a broad range of scattering angles (and including relatively high scattering angles) allows more scattered light to be detected than an arrangement in which a plurality of separate detectors are used to detect light scattered over a similar angular range.

The detector may comprise a focal plane array. The plane of the detector may be substantially normal to the light beam axis. This arrangement makes alignment of the detector more straightforward.

The collecting lens may have an optical axis, and the collecting lens may be arranged with its optical axis substantially co-incident with the light beam axis. This arrangement makes it straightforward to align the collecting lens, and also makes it more straightforward to optimise the performance of the optics.

The detector may comprise detector elements arranged to detect light scattered from the sample that has not passed through the collecting lens.

Particle characterisation may comprise determining a distribution of particle sizes.

The scattered light may leave the sample cell via the first wall and/or the second wall. The scattered light may leave via the convex external surface of the first wall and/or second wall. Scattered light leaving the sample cell via the second wall may be forward scattered light. Scattered light leaving the sample cell via the first wall may be backward scattered light. Forward scattered light may be defined as light scattered at angles of greater than 0° but less than 90° to the illuminating light beam axis. Back scattered light may be defined as light scattered at angles of greater than 90° (up to) 180°. Light referred to as at "a back scattering angle of x", where x is less than 90°, will be understood to refer to a scattering angle of 180°−x with respect to the illuminating light beam axis (with 0° in the direction of illumination).

Preferably, the external surface of at least the second wall is convex. Curving the external surface of the second wall allows light to escape from the sample cell that would otherwise have been totally internally reflected at the sample cell/air interface. Curving the external surface of either the first wall or the second wall enables the first or second wall of the sample cell to act as a lens. A sample cell with a first wall having a curved external surface can be used to eliminate a lens element or lens group that may otherwise have been necessary between the light source and the sample. A sample cell with a curved external surface can be used to compensate for increases in scattering angle caused by refraction of light at the sample cell/air interface (this applies equally to forward and backscattered light).

A convex external surface on a wall of the sample cell can be used to substantially prevent total internal reflection at high scattering angles. This totally internally reflected light is a source of optical noise. Reducing the reflected light improves the signal to noise ratio of the apparatus. A further technical effect of preventing total internal reflection at high scattering angles is to enable the detection of bubbles in liquid dispersions by allowing detection of the relatively intense scattering at high scattering angles due to total internal reflection at the liquid/bubble interface.

A sample cell in which the second wall has a curved external surface can be configured to reduce the divergence of a beam exiting the sample cell (i.e. as a converging lens). The reduced divergence of scattered light means that the scattered light is more concentrated, resulting in higher signal to noise ratios for a given solid angle over which a detector may receive light. An increased intensity of illumination of the sample may also be achieved by allowing a fixed diameter of illumination within the cell to be illuminated from a broader range of angles without an associated penalty in the size of the associated collection optic.

Curving the external surface of the sample cell can eliminate corners over a broad range of angles of incidence. This enables a large number of light sources and detectors to be arrayed around the device, and facilitates analysis using a wide range of optical techniques in a single instrument.

The first wall and/or second wall may comprise a lens. The lens is preferably a converging lens. The lens may be plano-convex. The lens may have a lens axis, about which the lens has rotational symmetry. The lens may be a doublet lens. A doublet lens can be configured to have reduced spherical aberration compared to a single simple lens element. The doublet lens may comprise a meniscus lens element bonded to a plano-convex lens element. The convex surface may be curved in two directions. The convex surface may be substantially spherically curved, or may be aspherically curved.

The lens axis of the first and/or second wall may be at an angle of less than 20 degrees to the illuminating light beam axis.

Aligning the sample cell with the illuminating light beam in this way reduces Fresnel reflections of the illuminating beam at the interfaces of the sample cell, thereby reducing optical noise and improving the optical signal to noise ratio. The present applicant has appreciated that the use of a cell wall with a convex surface allows light scattered at relatively high angles to escape from the cell without the need for inclining the cell at a relatively high angle to the incident light beam. This ability of a sample cell comprising a lens to facilitate light scattered at higher angles to escape from the sample cell has not hitherto been appreciated in the context of particle analysis based on detection of scattered light. Although US 2008/0221711 discloses the use of prisms to reduce high angle Fresnel reflections at the sample cell/air interface, it is not appreciated or taught therein that an arrangement in which a sample cell wall is a convex lens obviates the need to incline the cell at a relatively high angle. Shaping of the sample cell/air interface is disclosed as advantageous only in the context of reducing Fresnel reflections, not to facilitate light scattered at a higher range of angles to escape from the sample cell.

In some embodiments the second wall may be configured to allow light scattered from the sample at scattering angles of 10 degrees or less to at least 50 degrees to the incident light beam (or 5 degrees or less to at least 80 degrees, 0.5 degrees or less to at least 50 degrees) to escape from the external surface of the second wall of the sample cell without total internal reflection at the external surface of the second wall, when the sample comprises particles in a water dispersant. Increasing the range of scattering angles that can escape from the sample cell improves the ability of the apparatus to characterise smaller particles.

The first wall of the sample cell may be configured to collimate the light beam passing through the sample. This so called Fourier configuration provides unique transposition from the scattering angle to a detector location. Using the first wall of the sample cell as a collimating lens removes the need for a collimating lens external to the sample cell, and reduces the size of the instrument.

The first wall may be configured to focus the light beam within the sample and/or to form the light beam into a narrow beam within the sample, wherein the narrow beam has a maximum $1/e^2$ width that is less than half the distance across the interior of the sample cell along the light beam axis, or less than 20%, 10%, 2%, 1% of the distance across the interior.S The first wall and/or the second wall of the sample cell may comprise a substantially planar internal surface opposite the respective convex external surface.

The first and second wall may have substantially planar internal surfaces that are substantially mutually parallel.

The sample cell may be configured such that the first wall and second wall are separable, so that the internal surfaces of the sample cell can be cleaned.

The detector may be configured to detect scattered light leaving the sample cell via the first wall of the sample cell or the second wall of the sample cell. A further detector may be provided, configured to detect scattered light leaving the sample cell via the other wall of the sample cell.

The first and/or second wall of the sample cell may be configured to focus scattered light on the detector. The first and/or second wall of the sample cell may be configured to focus scattered light on the detector without an intermediary collecting lens.

The collecting lens element may have an axis that is substantially co-incident with the light beam axis. The collecting lens element may be configured to allow the light beam to bypass the collecting lens element.

The collecting lens element may be substantially sector shaped, when viewed along the lens element axis. The term substantially sector shaped, as used herein (in each and every aspect of the invention), includes a circular sector and an annular sector, and encompasses any shape with an arc shaped outer edge between two substantially radial edges The apparatus may comprise a further detector; wherein the further detector is arranged to detect light scattered at a first range of scattering angles, and the collecting lens element is configured to collect and focus scattered light scattered at a second range of scattering angles onto the detector (but not the further detector), wherein the second range of scattering angles is different from the first range, and wherein the plane of each of the detector and further detector is substantially normal to the light beam axis.

Each of the detector and the further detector may be arranged to detect forward scattered light.

The detector may be positioned closer to the sample cell than the further detector. In some embodiments, the detector and further detector may be arranged on the same plane. The detector and further detector may thereby be combined into a single planar detector.

The apparatus may comprise a first optical group configured to collimate the light beam in the sample, and a second optical group configured to direct forward scattered light towards the detector, wherein the detector is planar, the forward scattered light comprising a light scattered by interactions with the sample at a range of scattering angles and passing through the second wall. The forward scattered light is preferably collected and focused by the second optical group at the plane of the detector.

The optical power of the first and second wall may be substantially identical. The optical power of the first and second wall may be different. The optical power of the first wall may be less than the optical power of the second wall, which may be appropriate for collimating a light source with a low numerical aperture (such as a spatially filtered HeNe laser). A first wall with a relatively high positive optical power may be used to collimate a light source with a high numerical aperture. Such an arrangement conveniently facilitates the use of a relatively low cost, high power diode laser.

The apparatus may comprise a first optical group configured to direct the light beam into the sample, and a second optical group configured to collect and focus forward scattered light at the detector, wherein the detector is planar, and the forward scattered light comprises light scattered by interactions with the sample at a range of scattering angles and passing through the second wall. Configuring the apparatus so that a planar detector can be used to detect light scattered at a relatively broad range of angles facilitates a low cost design, by eliminating the need for a plurality of individually aligned detectors, each with their own optical element(s) and electrical connections.

The first optical group may comprise the first wall of the sample cell, and/or the second optical group may comprise the second wall of the sample cell. This saves cost and volume by eliminating the need for additional optical elements between the light source and sample and the sample and detector respectively.

The apparatus may comprise a further detector configured to detect backscattered light, the backscattered light comprising light scattered by interactions with the sample at a range of scattering angles and passing through the first wall, wherein the further detector is planar, and the further detector and first optical group are configured such that backscattered light at a range of scattering angles is aggregated and focused by the first optical group at the further detector.

The second optical group may be configured to direct the forward scattered light so that it is substantially normally incident with the detector and/or the first optical group is configured to direct the back scattered light so that it is substantially normally incident with the further detector. Directing the light normal to the detector or further detector maximises the light intensity for a given unit area of the detector, maximising the signal to noise ratio.

The (relatively broad) range of scattering angles for the forward scattered light and/or backscattered light may be at least 45 degrees. The range of scattering angles is preferably selected from the group of: at least 30 degrees, at least 45 degrees, at least 60 degrees, and at least 80 degrees.

The detector and/or further detector may be configured to receive scattered light at the range of scattering angles over an azimuthal range of at least 180 degrees. The range of azimuthal angles is preferably selected from the group of: at least 180 degrees, at least 270 degrees, at least 330 degrees and substantially 360 degrees. The increase in the range of azimuthal light collected increases the total signal, thereby increasing the signal to noise ratio.

The detector and/or further detector may comprise a monolithic focal plane array including a plurality of light detectors. The focal plane array may include a substantially sector shaped portion, which may be segmented into a plurality of annular detectors. This avoids the need for electrically connecting and aligning a plurality of detectors on a substrate. Furthermore, a monolithically integrated array of detectors can be provided with a smaller detector pitch, and can include integrated readout electronics and processing to minimise electronic noise. It is more straightforward to include such functionality on a relatively large array. Parasitic capacitance and inductance from electrical interconnections is also reduced, tending to improve the signal quality by reducing electrical noise.

The first and second optical group may be substantially symmetric about the centre of the sample. The first and/or second optical group may be rotationally symmetric about the light beam axis. The first and second optical group may have mirror symmetry about a line or plane passing through the centre of the sample. The line (or plane) may be orthogonal to the light beam axis. This provides an elegant optical solution which can easily be scaled. A symmetric arrangement is particularly suitable for directing a collimated light beam through the sample.

The first and/or second optical group may consist of four elements. Each element of the first and/or second optical group may comprise a plano-convex element. This has been found to be a particularly suitable arrangement that balances size, performance and cost.

The detector may be disposed adjacent to and parallel with a planar face of an element of the second optical group. The use of a lens element with a planar face adjacent to the detector means that it is straightforward to align and position the detector with respect to the optical element, for instance by offsetting it from the adjacent lens element using spacers.

The apparatus may be operable to employ a plurality of different optical measurement techniques, each optical measurement technique having its own respective light source and optical path for illuminating the sample. This may be particularly useful for a high value, small volume sample, where it is desirable to carry out a number of experiments in a short time.

The first and second wall may both comprise a converging lens, with the second wall having a higher optical power than the first wall.

Where the second wall comprises a convex surface, the chord height of the convex surface may comprise less than 75% of the total thickness of the second wall. The chord height may comprise less than 50% of the total thickness of the second wall.

Distinguishing bubbles from particles may comprise comparing a ratio of forward scattered light to back scattered light, wherein the forward scattered light has a scattering angle of at least the predetermined angle. Ratios above a predetermined size may indicate that bubbles are present in the sample. Bubbles may be detected if the ratio is greater than a 5, 10, 15 or 20.

The apparatus may comprise a processor configured to distinguish light scattered from bubbles in the sample from light scattered from particles in the sample by detecting stronger scattering from bubbles due to reflections therefrom at a range of scattering angles of more than a predetermined angle from the light beam axis; wherein the predetermined angle is at least 35 degrees.

According to a second aspect of the invention, there is provided a sample cell for use in an apparatus according the first aspect of the invention, the sample cell having at least one curved external wall. The sample cell may include any of the sample cell features described in other aspects or embodiments.

According to a third aspect of the invention, there is provided a method of distinguishing between bubbles and particles in a sample comprising a liquid, comprising illuminating the sample with a light beam along a light beam axis, detecting light scattered by the sample at a range of scattering angles, and distinguishing bubbles from particles in the sample by detecting the stronger scattering from bubbles due to reflections therefrom at a range of scattering angles of more than a predetermined angle from the light beam axis; wherein the predetermined angle is at least 35 degrees.

Distinguishing bubbles from particles may comprise comparing a ratio of forward scattered light to back scattered light, wherein the forward scattered light has a scattering angle of at least the predetermined angle. Ratios above a predetermined size may indicate that bubbles are present in the sample. Bubbles may be detected if the ratio is greater than a 5, 10, 15 or 20. The method may comprise determining when bubbles contribute to the scattered light from the sample. The contribution to scattering from bubbles may be removed or compensated for in the characterisation of particles by the apparatus, based on the detected scattered light. For example, the output of the detector may be ignored or given reduced weight during periods when it is determined that scattered light from a bubble is detected.

Alternatively or additionally, the method may comprise indicating to a user whether bubbles were present during a measurement, and may include indicating a measure of the quantity of bubbles (such as the number of bubbles, the fraction of measurement time when bubbles were present, or some other measure of the amount of bubbles). The user may then adjust the sample preparation or measurement conditions to ameliorate the presence of bubbles, for example by adjusting parameters such as: duration or intensity of sonication, stirring, temperature, circulation, degassing. The apparatus may be configured to automatically adjust sample preparation and measurement conditions to reduce the occurrence of bubbles during measurement.

The ratio of forward scattered light to back scattered light may be determined with reference to forward scattered light at scattering angles of between 40° and 60° from the light beam axis.

The predetermined angle may be selected from the group of: 40°, 50°, 60°, 70° and 80°.

The sample may comprise particles dispersed in water.

The light beam axis may pass through a first wall of the sample cell, through the sample, and through a second wall of the sample cell; wherein the first wall and/or second wall of the sample cell comprise a convex external surface through which the light beam axis passes.

The sample cell may comprise a planar external surface with a surface normal at an angle of at least 15° to the light beam axis, the planar external surface being arranged to allow light scattered at high angles to escape and be detected by the detector without total internal reflection at the external surface.

The sample cell may comprise a convex external surface. The sample cell may comprise a first and/or second wall that comprises a plano-convex lens.

The method may comprise monitoring scattered light from the sample, before it is averaged, for signals that are indicative of a large particle. When scattered light indicative of a large particle is detected, the method may comprise checking for light scattered at angles above the predetermined angle to determine whether the signals indicate a large particle or a bubble.

According to a fourth aspect of the invention, there is provided apparatus for distinguishing between bubbles and particles in a sample comprising a liquid, comprising means for illuminating the sample with a light beam along a light beam axis, and means for detecting light scattered by the sample at a range of scattering angles, and means for distinguishing bubbles from particles in the sample by detecting stronger scattering from bubbles due to reflections therefrom at a range of scattering angles of more than a predetermined angle from the light beam axis.

According to a fifth aspect of the invention, there is provided a particle characterisation apparatus comprising: a light source; a sample cell; a detector; and a processor; wherein the light source is operable to illuminate a sample comprising particles dispersed in a liquid within the sample cell with a light beam along a light beam axis, the light beam axis passing through the sample cell and the sample therein, so as to produce scattered light by interactions with the sample; wherein the detector is configured to detect scattered light leaving the sample cell at angles of at least a predetermined angle from the light beam axis; and the processor is configured to use the output of the detector to distinguish bubbles from particles in the sample by the stronger scattering from bubbles due to reflections therefrom at angles of more than the predetermined angle from the light beam axis; wherein the predetermined angle is at least 35 degrees.

The processor may be configured to distinguish bubbles from particles by determining a ratio of forward scattered light to back scattered light, wherein the forward scattering light has a scattering angle of at least the predetermined angle.

The processor may be configured to detect bubbles in the sample if the ratio is greater than 5, 10, 15, or 20.

The processor may be configured to determine the ratio of forward scattered light to back scattered light with reference to forward scattered light at scattering angles of between 40° and 60°.

The predetermined angle may be selected from the group of: 40°, 50°, 60°, 70° and 80°.

The sample may comprise particles dispersed in water.

The light beam axis may pass through a first wall of the sample cell, through the sample, and through a second wall of the sample cell; wherein the first wall and/or second wall of the sample cell comprise a convex external surface through which the light beam axis passes.

The sample cell may comprise a planar external surface with a surface normal at an angle of at least 15° to the light beam axis, the planar external surface being arranged to allow light scattered at high angles to escape and be detected by the detector without total internal reflection at the external surface.

The method of the third aspect of the invention may comprise using the apparatus according to any other aspect to distinguish bubbles from particles by detecting scattering therefrom. The apparatus of the fourth or fifth aspect may be configured to perform the method of the third aspect, including any or all of the optional features thereof.

According to another aspect of the invention, there is provided a computer readable medium, comprising software which is operable to identify bubbles in a liquid sample by determining a ratio of forward scattered light at scattering angles above a predetermined angle to back scattered light, wherein the predetermined angle is at least 35 degrees, and wherein bubbles are identified if the ratio is greater than 10.

According to a sixth aspect of the invention, there is provided a particle characterisation apparatus comprising: a light source; a sample cell; an optical group; and a detector; wherein the light source is operable to illuminate a sample within the sample cell with a light beam along a light beam axis, the light beam producing scattered light by interactions with the sample; wherein the optical group is configured to collect and focus scattered light on the detector, and comprises at least one lens element; wherein a lens element of the optical group comprises an open region along the lens element axis, and the lens element is positioned with its axis substantially coincident with the light beam axis so that the light beam passes through the open region.

This arrangement reduces stray light within the apparatus as a result of reflection of the light beam from the surfaces of the lens element. The light beam is typically many orders of magnitude more powerful than the scattered light from the sample, and reflection of even a small proportion of the light beam can result in considerable stray light, which results in optical noise that tends to mask scattered light from detection. The use of a lens element that is configured to allow the light beam to pass by or through it without reflection may substantially reduce optical noise. This may substantially improve the performance of optical configurations in which collecting lenses are on the axis of the light beam that would otherwise have resulted in the signal of the scattered light being swamped by reflections from the collection optics.

The lens element may be formed from circular lens element with a central through hole co-incident with the axis of the lens.

The lens element may be substantially sector shaped when viewed along the lens element axis. The shape of the lens may correspond with a region of a circular lens element. The region may correspond with part of a sector of the circular lens element (viewed along the axis of the circular lens element). The sector shaped lens element may comprise a first face formed by cutting a circular parent lens along a first radius, and a second face formed by cutting a circular parent lens along a second radius.

The use of a sector shaped lens may provide for substantial economy in the production of collection lenses, wherein a single circular parent lens may be cut into a plurality of segment shaped lenses. Furthermore, the use of sector shaped lenses allows lenses positioned on the axis of the light beam to provide a plurality of differently configured optical paths for light scattered at different azimuthal scattering angles.

The sector shaped lens element may be formed from a circular lens element by cutting the circular lens element along a first and second radius.

The lens element may comprise an aspheric surface. It has been found that the use of aspheric surfaces considerably reduce the optical path length necessary to achieve acceptable performance.

The optical group may be configured to direct and focus forward scattered light at forward scattering angles of at least 35 degrees to the light beam axis, preferably at angles of a least 50 degrees to the light beam axis.

The optical group may comprise a plurality of lens elements, or may comprise a single lens element.

At least two lens elements of the optical group may comprise lens elements with an open region along their axis.

The optical group may comprise at least one substantially circular lens that does not include an open region along its axis. Regions of the optical path that are remote from the sample cell may need to collect a relatively diverged beam, and the use of a circular lens may therefore be more appropriate than a segment shaped lens.

The apparatus may comprise a further detector, wherein the detector is configured to detect light scattered at a first range of angles to the light beam axis, and the further detector is configured to detect light scattered at a second range of angles to the light beam axis. The first range may be broader than the second range. The first range may include a higher maximum scattering angle than the second range.

The optical group may be configured to produce an image spot on the detector with a radial extent that is less than half of a tangential extent of the image spot. It has been found that optimising lens design for radial spot size, while allowing the tangential spot size to be substantially unconstrained, results in a superior design for light scattering applications, where the scattering angle is more important than the azimuthal direction of scattering.

According to a seventh aspect of the invention, there is provided a lens element with an open region along the axis of the lens element, for use with the apparatus of any other aspect of the invention. The lens may be suitable for collecting scattered light and/or focussing scattered light at a detector. The lens may not include a reflective coating. The lens may comprise an aspheric surface. A surface of the lens may be coated with an anti-reflective coating. The lens may include any of the features taken from any lens with an open region along its axis in any aspect or embodiment of the invention.

According to an eighth aspect of the invention, there is provided a particle characterisation apparatus comprising: a light source; a sample cell; an optical group; and a detector; wherein the light source is operable to illuminate a sample within the sample cell with a light beam along a light beam axis, the light beam producing scattered light by interactions with the sample; wherein the optical group is configured to collect and focus scattered light on the detector and comprises at least one lens element; wherein a lens element of the optical group is substantially sector shaped when viewed along the lens axis.

The use of a sector shaped lens element substantially reduces the cost and weight of the system, without penalty in performance. Where an apparatus includes a detector configured to detect P-polarised light, or S-polarised light, or light at any selected range of azimuthal angles, a sector shaped lens can readily be used to direct light to the detector without loss of performance. A plurality of sector shaped lenses may be produced from a single circular lens blank after it has been ground and polished, by cutting it along radii (or diameters) thereby reducing the cost of each lens element.

It is not essential that a sector shaped lens comprise an open region for the light beam to pass through, because the sector shaped lens may be slightly offset from the light beam axis, or the sector shaped lens may be positioned behind a beam stop that stops the optical light beam.

A sector shaped lens element that is configured to allow the illuminating light beam to pass by can readily be created by forming a hole in a circular lens blank before the lens blank is cut into sector shaped lens elements.

The optical group may be configured to collect and focus, at the detector, light scattered over an azimuthal range of less than 90 degrees.

The apparatus may comprise a further detector, wherein the further detector is arranged to detect light scattered over a further azimuthal range that excludes the azimuthal range collected by the optical group.

The detector and/or further detector may be arranged to detect P-polarised scattered light, or S-polarised scattered light.

The detector may be configured to detect light scattered at a first range of elevation angles, and the further detector may be configured to detect light scattered at a second range of elevation angles. The first range may be broader than the second range. The first range may include a higher maximum scattering angle than the second range.

The segment shaped lens element may be formed from a circular lens element by cutting the circular lens element along a first and second radius.

The lens element may comprise an aspheric surface.

The lens element may be arranged with its axis substantially coincident with the light beam axis.

The optical group may be configured to direct and focus forward scattered light at angles of at least 35 degrees to the light beam axis, and preferably at angles of at least 50 degrees to the light beam axis.

The optical group may comprise a plurality of lens elements.

The optical group may be configured to produce an image spot on the detector with a radial extent that is less than half of a tangential extent of the image spot.

According to a ninth aspect of the invention, there is provided a substantially sector shaped lens element, for use with the apparatus of any other aspect of the invention. The lens may be suitable for collecting scattered light and/or focussing scattered light at a detector. The lens may not include a reflective coating. The lens may comprise an aspheric surface. A surface of the lens may be coated with an anti-reflective coating. The lens may include any of the feature of any lens that is sector shaped in any aspect or embodiment.

According to a tenth aspect of the invention, there is provided a particle characterisation apparatus comprising: a light source; a sample cell; a first detector, an optical group and a second detector; wherein the light source is operable to illuminate a sample within the sample cell with a light beam along a light beam axis, the light beam producing scattered light by interactions with the sample; wherein the first detector is arranged to detect forward scattered light scattered at a first range of scattering angles onto the first detector, and the second detector is arranged to detect forward scattered light scattered at a second range of scattering angles that is collected and focussed onto the second detector by the optical group, wherein the second range of scattering angles is different from the first range, and wherein the plane of each of the first detector and second detector is substantially normal to the light beam axis.

The optical group may collect and focus forward scattered light onto the second detector but not the first detector.

The first detector is preferably separate from the second detector, meaning that the second detector is not integrally formed with the first detector (e.g. part of the same focal plane array). The first and second detector may not be supported on a common planar substrate.

This arrangement allows detection of a broad range of scattering angles using two relatively compact planar detectors. The alignment of the detectors is relatively straightforward, because each of the detectors is substantially normal to the axis of the illuminating light beam. Furthermore, because each of the detectors is normal to the light beam, the collecting lens (or lenses) of the optical group may be positioned and oriented with their axis substantially co-incident with the axis of the illuminating light beam. The relatively continuous light field at the detectors means that this arrangement is relatively insensitive to misalignment of the lenses or detectors.

Prior art arrangements with a plurality of separate detectors (not integrally formed), each covering a relatively narrow range of scattering angles, are more problematic to align, because misalignment can result in the scattered light missing the detector at the edges. Consequently, oversized detectors tend to be used, which results in increased parasitic capacitance and increased noise. The reduced number of detectors and lens elements that are facilitated by aspects of the invention makes some embodiments more straightforward to electrically connect and to assemble.

The optical group may comprise at least one lens element having a lens axis that is substantially co-incident with the light beam axis. The optical group may comprise a single lens element.

The optical group may comprise at least one lens element and each of the at least one lens element may have a lens element axis that is substantially co-incident with the light beam axis.

The second range of angles may include a larger maximum scattering angle than the first range of angles.

The first and second range of angles may comprise mutually exclusive azimuthal angular ranges.

The light source may be configured to produce plane polarised light, and the azimuthal angular range of each of the first and second range of angles may be substantially centred on the polarisation plane, so that each of the first and second detector are arranged to detect P-polarised scattered light or S-polarised scattered light, or light scattered at any azimuthal range.

The apparatus may further comprise a diverging lens positioned between the first detector and the sample cell.

The first detector may be positioned at a different distance from the sample cell than the second detector. The first detector may be positioned closer to the sample cell than the second detector, or vice versa. The first and second detector may be at the same distance from the sample cell.

The optical group may comprise at least one lens that is substantially sector shaped.

The optical group may comprise at least one lens that is circular.

The optical group may comprise at least one lens element comprising an open region along the axis of the lens element, wherein the lens element is arranged to allow the light beam to pass through the open region thereof.

The optical group may be configured to provide a focussed spot size on the second detector that is at least twice as large in tangential extent as in radial extent.

The first detector may be arranged to detect light scattered over a first azimuthal range, and the second detector may be arranged to detect light scattered over a second azimuthal range, wherein the first azimuthal range excludes the second azimuthal range.

The optical group may comprise a lens element that comprises an aspheric surface.

The optical group may be configured to direct and focus forward scattered light at angles of: at least 15 degrees to the light beam axis, at least 35 degrees to the light beam axis, or at least 50 degrees to the light beam axis.

The apparatus may further comprise a third detector for detecting back scattered light from the sample.

According to another aspect of the invention, there is provided a particle characterisation apparatus comprising: a light source; a sample cell; and a detector; wherein the light source is operable to illuminate a sample within the sample cell with a light beam along a light beam axis, the light beam axis passing through a first wall of the sample cell, through the sample, and then through a second wall of the sample cell, thereby producing scattered light by interactions with the sample; wherein the detector is configured to detect scattered light leaving the sample cell; and wherein the narrow beam has a maximum $1/e^2$ width that is less than half the distance across the interior of the sample cell along the light beam axis.

The first wall and/or second wall of the sample cell may comprise a convex external surface through which the light beam passes. The first wall and/or second wall may comprise plano-convex lenses.

The apparatus may comprise an optical group configured to collect and focus scattered light on the detector. The optical group may comprise a lens element. The lens element may comprise an aspheric surface. The lens element may be sector shaped. The lens element may be configured to allow the light beam to bypass the lens element through an open region thereof. The lens element may be positioned with its axis substantially co-incident with the light beam axis.

In this configuration the light beam may be narrow enough to encompass only one, or a few large particles at a time, and the light scattered therefrom may therefore be gathered over a broad angular range (rather than a relatively narrow range of azimuth corresponding with P-polarised scattered light). The detector for each range of scattering angle may comprise an annulus with a circumferential extent of greater than 30, 45, 90 or 180 degrees.

According to another aspect of the invention, there is provided a particle characterisation apparatus comprising: a light source; a sample cell; and a detector; wherein the light source is operable to illuminate a sample within the sample cell with a light beam, thereby producing scattered light by interactions with the sample; wherein the detector is configured to detect scattered light leaving the sample cell; and further comprising a plurality of sample holders for containing a plurality of samples, the sample holders being moveable within the sample cell to position each sample within the sample cell for illumination.

According to another aspect of the invention, there is provided a particle characterisation apparatus comprising: a light source; and a sample cell; wherein the light source is operable to illuminate a sample within the sample cell with a light beam along a light beam axis, the light beam axis passing through a first wall of the sample cell, through the sample, and then through a second wall of the sample cell, thereby producing scattered light by interactions with the sample; and wherein the apparatus comprises a first optical group configured to direct the light beam into the sample, and a second optical group configured to collect and focus forward scattered light at a first planar detector, the forward scattered light comprising light scattered by interactions with the sample at a range of scattering angles and passing through the second wall; wherein the second optical group is configured to direct forward scattered light to be substantially normally incident with the first planar detector.

According to another aspect of the invention, there is provided a particle characterisation apparatus comprising: a light source; and a sample cell; wherein the light source is operable to illuminate a sample within the sample cell with a light beam along a light beam axis, the light beam axis passing through a first wall of the sample cell, through the sample, and then through a second wall of the sample cell, thereby producing scattered light by interactions with the sample; and wherein the apparatus comprises a first optical group configured to direct the light beam into the sample, and a second optical group configured to aggregate forward scattered light at a first planar detector, the forward scattered light comprising light scattered by interactions with the sample at a range of scattering angles and passing through the second wall; wherein the first detector is disposed adjacent to and parallel with a planar surface of the second optical group.

The apparatus may comprise a second detector configured to detect back scattered light collected by the first optical group. The second detector may be disposed adjacent to and parallel with a planar surface of the first optical group.

According to another aspect of the invention, there is provided a method of designing an optical arrangement for collecting and focussing scattered light on a detector in a particle characterisation apparatus, comprising minimising a radial spot size at the detector, without constraining a tangential spot size at the detector.

The optical arrangement may be part of an apparatus according to any of the other aspects of the invention. The scattered light may arise from the interaction of an illuminating light beam with a sample in a sample cell. The light beam may pass through a first wall of the sample cell, through the sample, and then through a second wall of the sample cell. The first wall and/or second wall may comprise a convex external surface. The first wall and/or second wall may comprise a plano-convex lens.

The optical arrangement may comprise a collecting lens arranged to collect scattered light and focus it on the detector. The radial and tangential directions may be defined with reference to the collecting lens axis. The radial direction may correspond with a line of fixed azimuth angle along a range of elevation angles (with respect to the collecting lens axis axis). The tangential direction may correspond with a line of fixed elevation angle along a range of azimuthal angles (with respect to the collecting lens beam axis).

The collecting lens may comprise an aspheric surface. The collecting lens may be substantially sector shaped when viewed along the lens axis. The collecting lens may be arranged with its optical axis substantially co-incident with the light beam axis. The collecting lens may comprise an open region along the collecting lens axis so that the light beam passes through the open region of the collecting lens. There may be more than one collecting lens. Each collecting lens may comprise an aspheric surface. The convex external surface of the second wall of the sample cell may be aspheric. The detector may comprise an arc shaped detector element. The detector may comprise a one-dimensional array of arc shaped detector elements.

Minimising spot size at the detector may comprise using a computer to perform a constrained optimisation of an optical design. The optical design may comprise a second wall of a sample cell that is configured as a lens, a collecting lens and a detector.

According to another aspect of the invention, there is provided a particle characterisation apparatus comprising: a light source; a sample cell; a collecting lens; and a detector; wherein the light source is operable to illuminate a sample within the sample cell with a light beam along a light beam axis, the light beam producing scattered light by interactions with the sample; wherein the collecting lens is configured to collect and focus forward scattered light onto the detector, and the collecting lens has an arc shaped point spread function at the detector.

According to another aspect of the invention, there is provided a particle characterisation apparatus comprising: a light source; a sample cell; a collecting lens; and a detector; wherein the light source is operable to illuminate a sample within the sample cell with a light beam along a light beam axis, the light beam producing scattered light by interactions with the sample; wherein the collecting lens is configured to collect and focus forward scattered light scattered onto the detector such that the tangential spot size at the detector is at least twice the radial spot size at the detector.

The light beam may pass through a first wall of the sample cell, through the sample, and then through a second wall of the sample cell. The first wall and/or second wall may comprise a convex external surface. The first wall and/or second wall may comprise a plano-convex lens.

The collection lens may comprise an aspheric surface. The collection lens may be substantially sector shaped when viewed along the lens axis. The collection lens may be arranged with its optical axis substantially co-incident with the light beam axis. The collection lens may comprise an open region along the collection lens axis so that the light beam passes through the open region of the collection lens. There may be more than one collection lens. Each collection lens may comprise an aspheric surface. The convex external surface of the second wall of the sample cell may be aspheric. The detector may comprise an arc shaped detector element. The detector may comprise a one-dimensional array of arc shaped detector elements. The plane of the detector may be substantially normal to the light beam axis.

The applicant has found that optimising lens design with the tangential spot size unconstrained results in highly compact designs with improved performance, compared with designs produced by the more conventional process of optimising for minimum spot size in both radial and tangential extent. A dispersion of the spot at the detector in the tangential direction will not smear the relationship between a scattering angle and a detector element. In contrast, dispersion in the radial direction at the detector will result in a smearing of the relationship between the scattering angle and the detector element to which it maps.

According to another aspect of the invention, there is provided a particle characterisation apparatus comprising: a light source; a sample cell; a first detector and a second detector; wherein the light source is operable to illuminate a sample within the sample cell with a light beam along a light beam axis, the light beam producing scattered light by interactions with the sample; wherein the first detector is configured to detect forward scattered light from the sample and the second detector is configured to detect back scattered light from the sample; wherein an internal surface of the sample cell is coated with an anti-reflective coating.

Coatings on internal surfaces of sample cells have not traditionally been used in the context of particle characterisation using scattered light. Light reflected at internal surfaces of the sample cell have not been a significant source of optical noise in prior art systems, where a greater contribution of optical noise may result from total internal reflection of light scattered at angles greater than the critical angle for a water/air interface. Concerns over potential contamination of the sample by the anti-reflective coating mean that a prejudice against such coatings has hitherto existed in the context of particle characterisation. The present applicant has found that coating an internal surface of the sample cell with an anti-reflective coating may result in a significant reduction in optical noise, particularly in back-scattered light. A synergy exists between such an anti-reflection coating on an internal surface of the sample cell and a sample cell comprising a convex external surface arranged to increase the range of scattering angles at which scattered light may leave the sample cell, because the contribution of reflections at this interface can be a more significant source of optical noise in such an embodiment.

The internal surface of the sample cell that is coated with an anti-reflective coating may be a surface through which forward scattered light leaves the sample cell. The present applicant has found that forward scattered light that is reflected at the internal interface of the sample cell may otherwise make a significant contribution to optical noise in back scattered light.

An external surface of the sample cell may be provided with an anti-reflective coating. It may be challenging to achieve a uniform coating thickness on a highly curved surface, but the applicant has identified that an anti-reflective coating with a variable thickness on a convex external surface of the sample cell may significantly improve performance. Angles of incidence at relatively high scattering angles are more nearly perpendicular at a convex external surface than would be the case in a cell with flat external surfaces, and the performance of an anti-reflection coating is therefore enhanced.

The light beam may pass through a first wall of the sample cell, through the sample, and then through a second wall of the sample cell. The first wall and/or second wall may comprise a convex external surface. The first wall and/or second wall may comprise a plano-convex lens.

The apparatus may comprise a collection lens for collecting and focussing scattered light on the first or second detector. The collection lens may comprise an aspheric surface. The collection lens may be substantially sector shaped when viewed along the lens axis. The collection lens may be arranged with its optical axis substantially co-incident with the light beam axis. The collection lens may comprise an open region along the collection lens axis so that the light beam passes through the open region of the collection lens. There may be more than one collection lens. Each collection lens may comprise an aspheric surface. The convex external surface of the second wall of the sample cell may be aspheric. The first and/or second detector may comprise an arc shaped detector element. The first and/or second detector may comprise a one-dimensional array of arc shaped detector elements. The plane of the first and/or second detector may be substantially normal to the light beam axis. The first and second detector may be disposed in different azimuthal locations, with respect to the light beam axis, such that the second detector substantially avoids reflected forward scattered light from the first detector.

According to another aspect of the invention, there is provided a particle characterisation apparatus comprising: a light source; a sample cell; a first detector and a second detector; wherein the light source is operable to illuminate a sample within the sample cell with a light beam along a light beam axis, the light beam producing scattered light by interactions with the sample; wherein the first detector is configured to detect forward scattered light from the sample and the second detector is configured to detect back scattered light from the sample; wherein the first detector is disposed in a different azimuthal region than the second detector, such that the second detector substantially avoids forward scattered light reflected from the first detector.

The term "azimuthal region" refers to a range of azimuthal angles with respect to the light beam axis.

Reflections of forward scattered light from the first detector may comprise a significant component of optical noise in the back scattering direction, and avoiding this noise may result in a substantial improvement in signal to noise ratio for back scattered light detection.

The first detector may be arranged to detect substantially S-polarised light, and the second detector may be arranged to detect substantially P-polarised light. Alternatively, the first detector may be arranged to detect substantially P-polarised light, and the second detector may be arranged to detect substantially S-polarised light. The first detector may be offset from the second detector by between 45° and 135° in azimuth (with respect to the light beam axis), or by between 75° and 115°, or by substantially 90°.

A normal direction from a detecting surface of the first detector may be substantially parallel to a normal direction from a detecting surface of the second detector.

The first and second detector may each be arranged with their surface substantially normal to the light beam axis. The first and/or second detector may comprise a focal plane array including a plurality of integrally formed light detectors. The focal plane array may include a substantially sector shaped portion, which may comprise a plurality of annular detectors.

The light beam axis may pass through a first wall of the sample cell, through the sample, and through a second wall of the sample cell. The first and/or second wall may comprise a curved external surface. The first and/or second wall may comprise a plano-convex lens. An internal surface of the second wall may be coated with an anti-reflection coating to reduce reflections at the sample/second wall interface. The convex external surface of the first and/or second wall may be coated with an anti-reflection coating to reduce reflections at the sample cell/air interface. The first detector and/or second detector may be coated with an anti-reflection coating.

Each aspect of the invention can be advantageously combined with each other aspect of the invention. Each optional feature of each aspect can similarly be advantageously applied to each other aspect of the invention. For instance, a sample cell comprising a convex external surface may be employed in each aspect. A sector shaped collection lens may be used in all aspects. A collection lens with an open region along the lens axis for an illuminating beam for light to pass through may be used with all aspects.

The invention will now be described, by way of example, with reference to the following drawings, in which.

Figure 42:
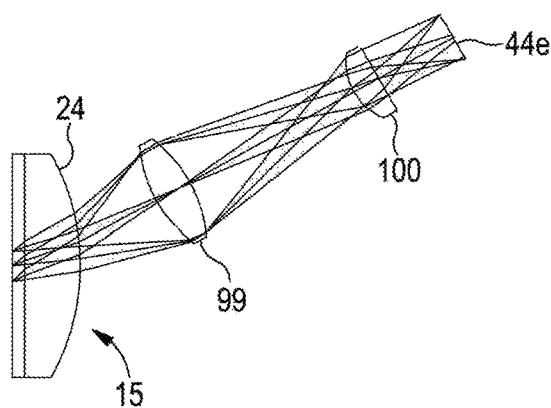
FIG. 42 is a ray diagram of a Köhler type discrete back scatter detection channel according to an embodiment.
Figure 43:
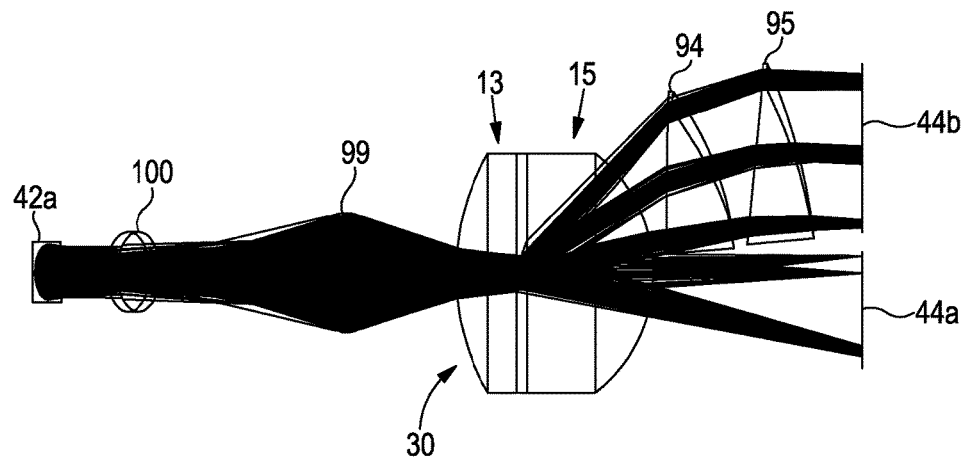
FIG. 43 is a ray diagram of an embodiment that includes the Köhler type discrete back scatter channel.
Figure 44:
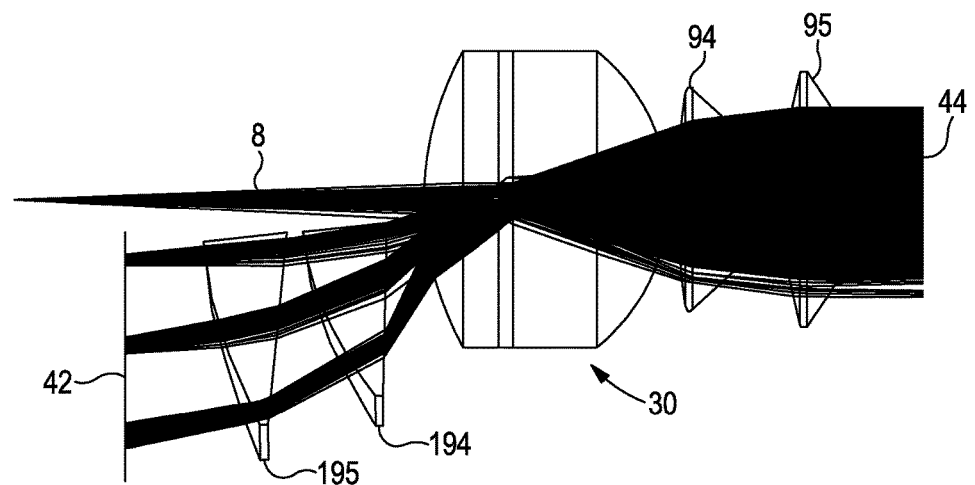
FIGS. 44 and 45 are ray diagrams of an embodiment comprising the forward scatter detection arrangement of FIG. 33, with a back scatter collection arrangement comprising a pair of lenses and a detector that correspond with the lenses and detector of the forward scatter arrangement.
Figure 45:
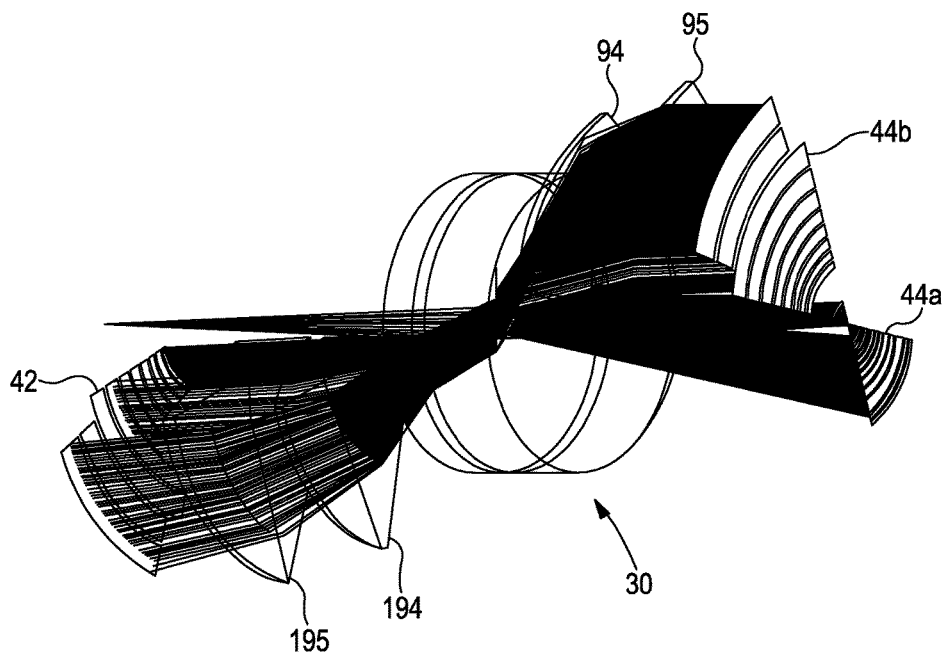
Figure 46:
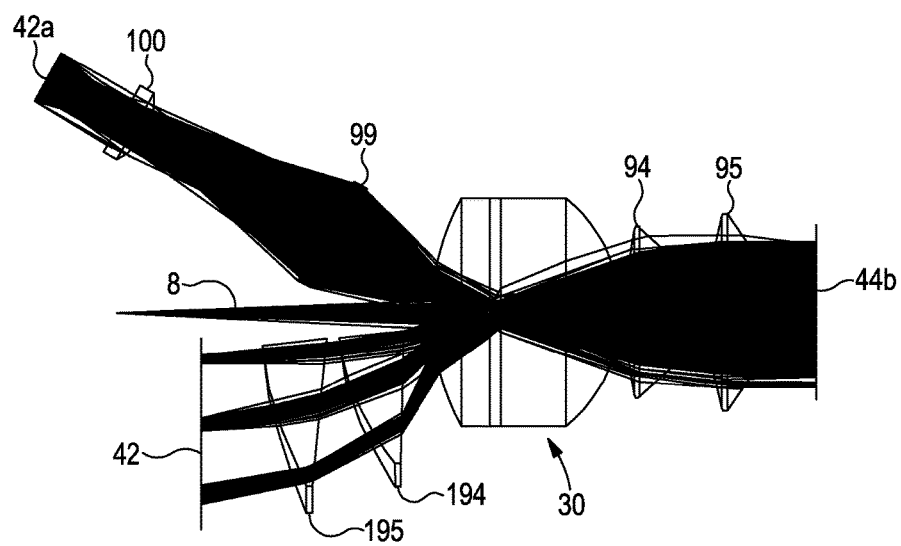
Figure 47:
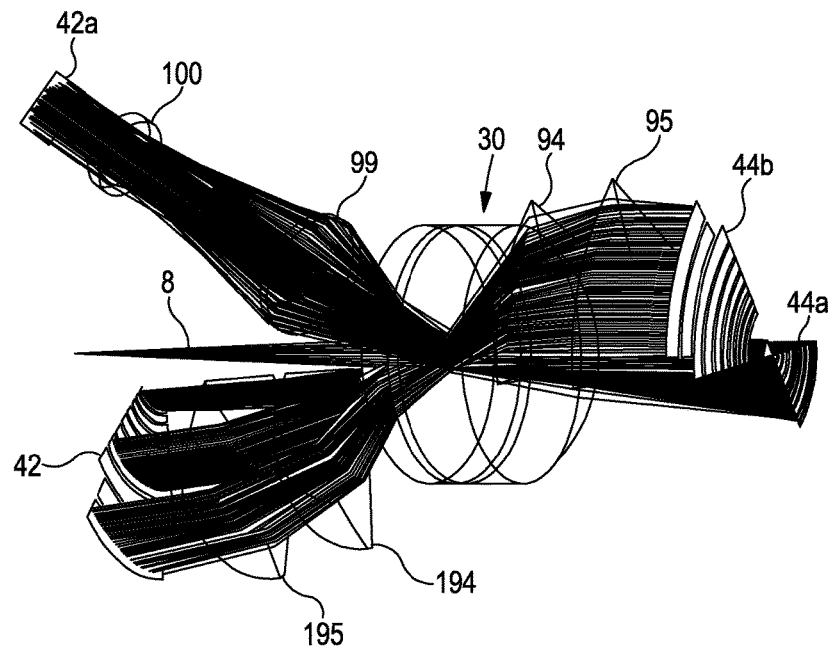
Figure 48:
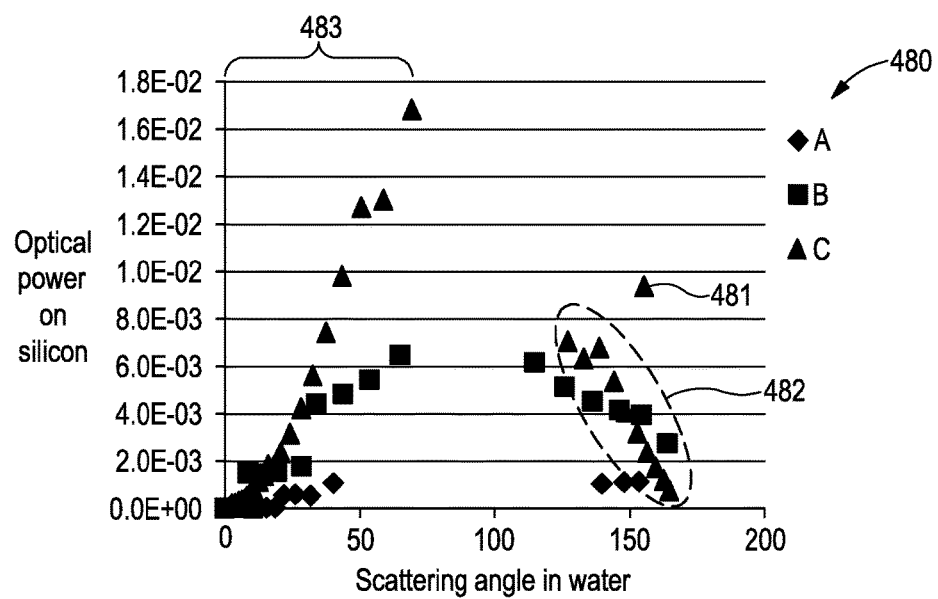
Figure 49:
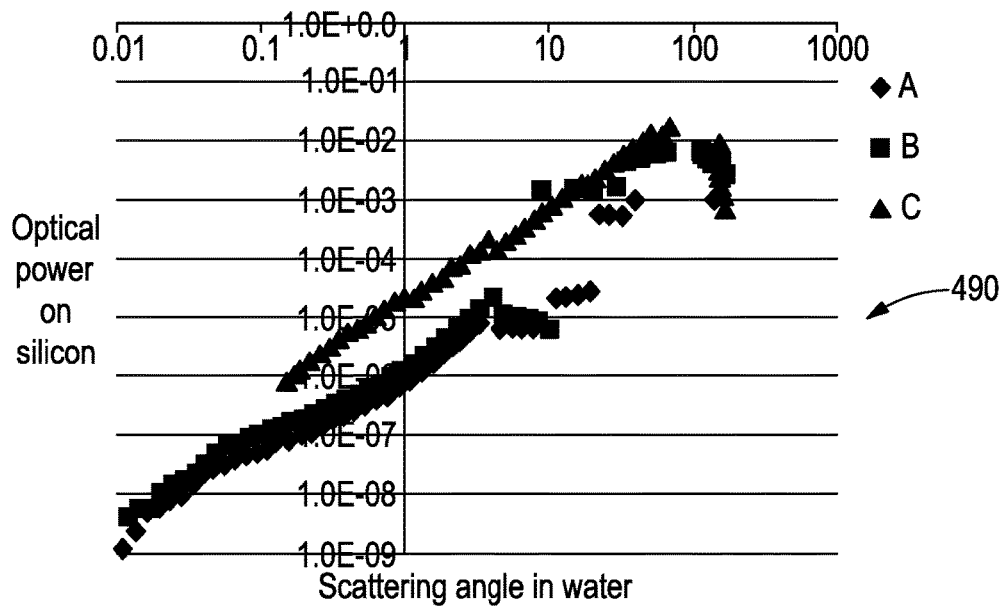
Figure 50:
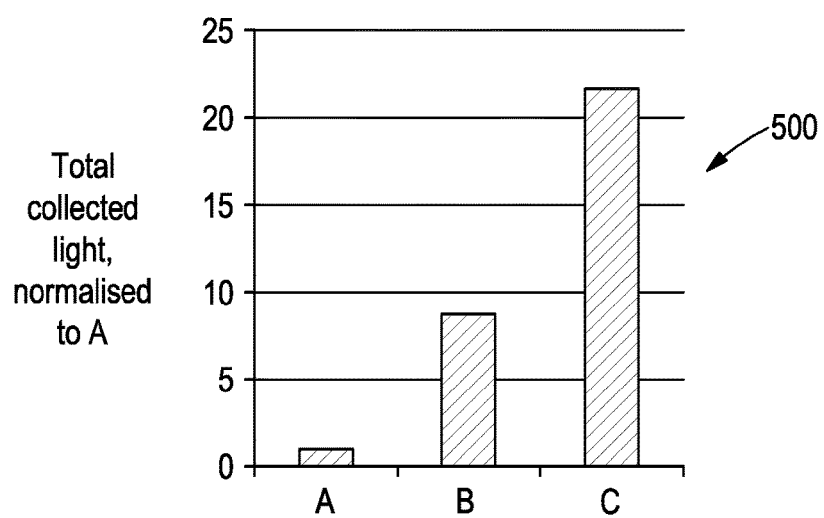
Figure 51:
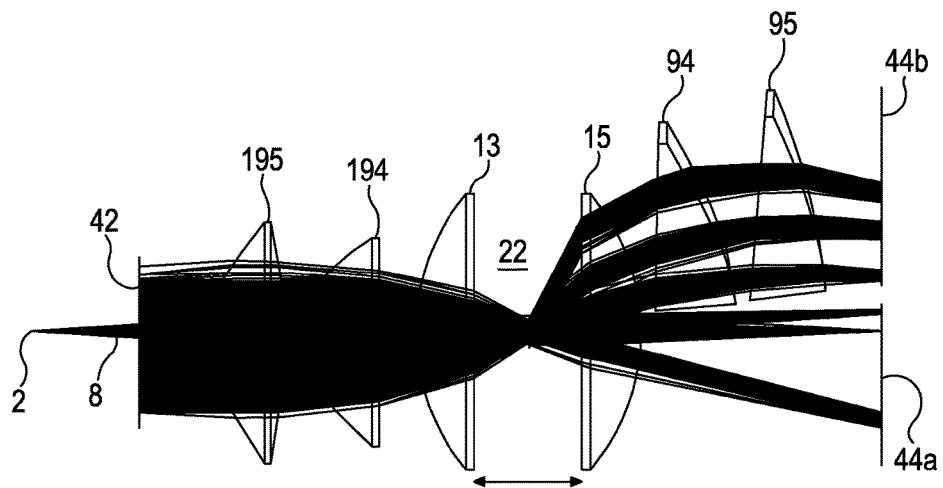
Figure 52:
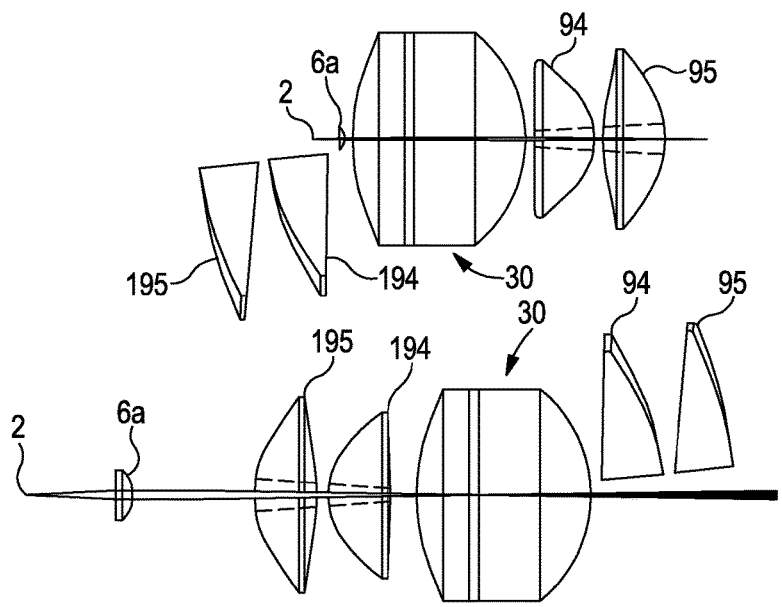
Figure 53:
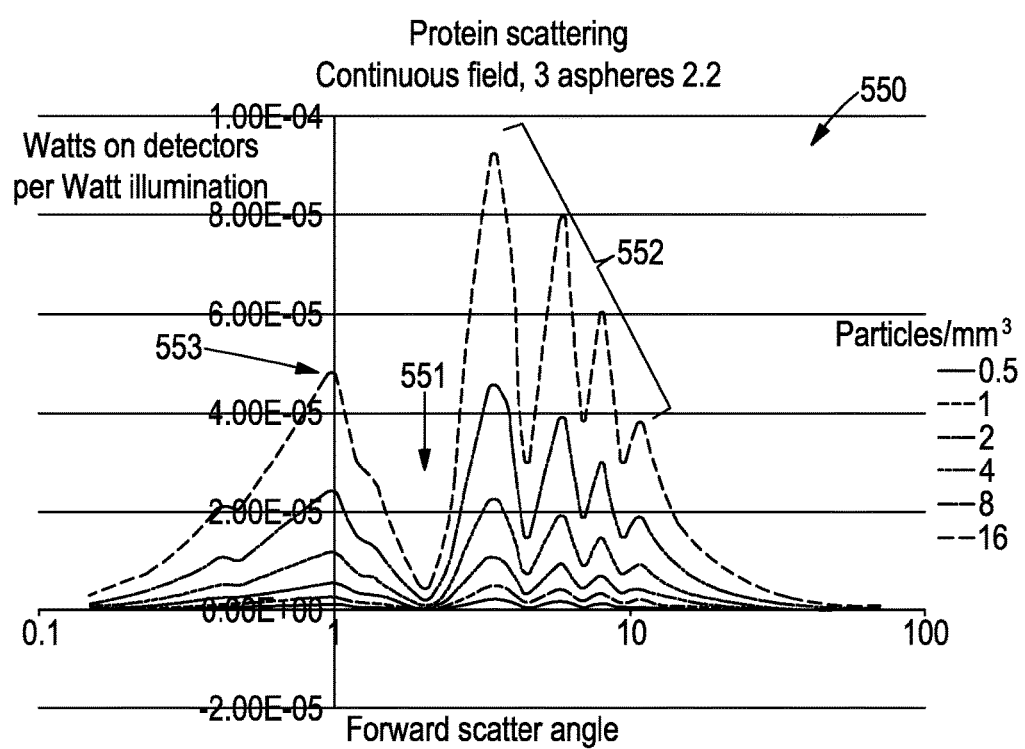

FIGS. 46 and 47 are ray diagrams of the embodiment of FIGS. 44 and 45, further comprising the Köhler type discrete backscatter detection channel of FIGS. 42 and 43;

FIGS. 48 and 49 are graphs comparing the optical power at the detector for a range of scattering angles for: (A) a prior art arrangement; (B) the embodiment of FIG. 3; and (C) the embodiment of FIGS. 46 and 47;

FIG. 50 is a bar graph comparing the total collected light at the detector for (B) and (C) with that of the prior art arrangement (A);

FIG. 51 is a ray diagram of a modified version of the embodiment of FIGS. 44 and 45, wherein the sample cell has been replaced with a sample cell for a sample in which particles are dispersed in air;

FIG. 52 is ray diagram of two embodiments in which the illuminating beam width is narrow within the sample; and FIG. 53 is a graph showing the detection of light scattering from proteins in accordance with the invention.

Figure 1:
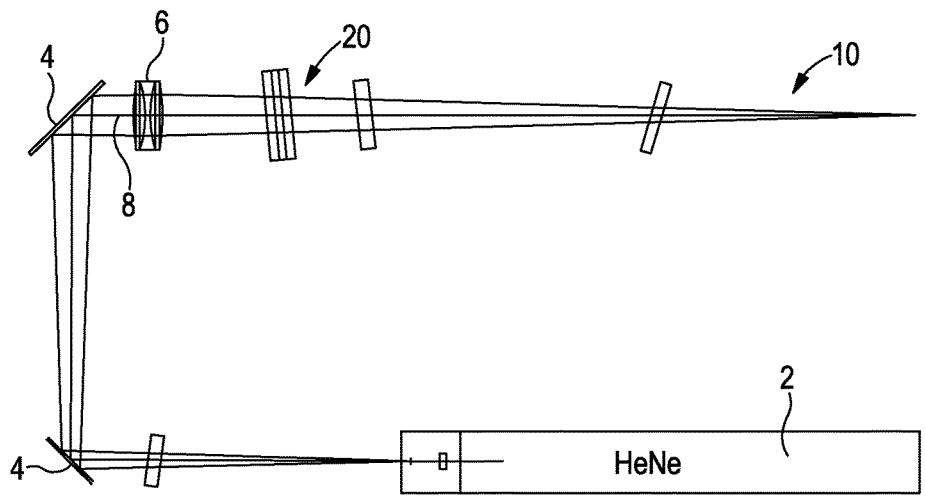
FIG. 1 is a schematic of a prior art particle characterisation apparatus.

Referring to FIG. 1, a prior art apparatus 10 for particle characterisation is shown, comprising a light source 2 for illuminating a sample cell 20 with a light beam 8. The apparatus 10 further comprises a plurality of detectors (not shown) for detecting light scattered from a sample inside the sample cell 20. The light source 2 is a Helium Neon laser, which is relatively large. A first mirror 4 and second mirror 4 are used to fold the optical path of the light beam 8 through two 90 degree bends so that the light source 2 can be accommodated below the optical path of the light beam 8 through the sample. This provides for a relatively compact apparatus, but can lead to indirect heating of the sample by the light source, for example by convective heat transfer. A triplet lens 6 is provided between the second mirror 4 and the sample cell 20 to provide the necessary beam quality through the sample. The light beam 8 converges through the sample.

Figure 2:
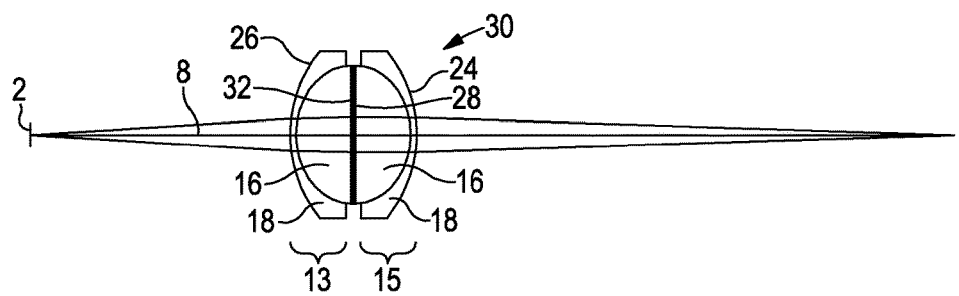
FIG. 2 is a schematic showing a light beam path from a light source through a sample cell, for an apparatus according to a first embodiment of the invention.

FIG. 2 shows a sample cell 30 according to an embodiment of the invention, under illumination from a light source 2. The sample cell 30 houses a sample 22, and comprises a first wall 13 through which the light beam illuminates the sample, and a second wall 15 from which the light beam 8 exits the sample, absent any scattering in the sample.

The first wall 13 comprises a convex external surface 26 and an opposing planar internal surface 32. The difference in curvature between the opposing internal and external surface of the first wall 13 mean that it is configured to act as a lens element. The first wall 13 and second wall 15 of the sample cell 30 are substantially symmetric about the centre of the sample 22. The second wall 15 similarly comprises a convex external surface 24 and an opposing planar internal surface 28. The planar internal surfaces 32, 28 of the first and second wall are adjacent and substantially parallel and define a flow channel through which a dispersant (e.g. water) carrying particles can flow. The sample cell 30 can be disassembled for cleaning of the internal surfaces 32, 28 of the first and second wall 13, 15. The first wall 13 is separable from the second wall 15.

The first and second wall of the sample cell 13, 15 each comprise a doublet lens. The first wall 13 and the second wall 15 each respectively comprise a meniscus first lens element 18 bonded to a plano-convex second lens element 16. The first lens element 18 of each of the first and second wall 13, 15 respectively comprise the respective external surface 26, 24, and the second lens element 16 of the first and second wall respectively comprise the planar internal surface 32, 28. This doublet arrangement reduces spherical aberration, which can become problematic if the optical power of the sample cell is sufficiently high.

The curvature of the external surface 26 of the first wall 13 allows a light source 2 with a low numerical aperture to be used, and in this embodiment the light source 2 is a laser diode. Laser diode lasers are relatively cheap, and can provide high power in a compact volume. Furthermore, the triplet lens that was necessary in the prior art arrangement of FIG. 1 between the light source and the sample cell has been eliminated, with the optical power now provided by the first wall 13 of the sample cell 30. The geometry of the flow channel through the sample cell 30 is unchanged.

Eliminating lenses that were previously between the light source and the sample cell reduces scatter from optical surfaces by reducing the number of optical surfaces in the apparatus, thereby reducing optical noise. The improved collection efficiency that is possible according to some embodiments allows a smaller light source to be used, which can be packaged to avoid indirect heating of the sample by the light source (for example by convection). This reduces the creation of bubbles in the sample (when the sample comprises a water dispersant) due to outgassing, reduces the time to warm the sample to equilibrium (so as to eliminate thermal gradients etc).

In prior art devices (such as that shown in FIG. 1) the beam tends to be convergent through the cell. The sample thickness places a blur on the transposition between the scattering angle to the position of the detector, which can become significant where the dispersant is air. In such cases the sample thickness may be about 10 mm. The arrangement of the first embodiment has an equal distribution of optical power on either side of the sample 22, resulting in a light beam through the sample that is well collimated (parallel, or near-parallel). This Fourier configuration leads to a unique transposition between the scattering angle and a detector position.

The second wall 15 is configured to allow light scattered from the sample at angles of 0 to 80 degrees to the incident light beam 8 to escape from the external surface 24 of second wall 15 of the sample cell 30 without total internal reflection at the external surface 24, when the sample 22 comprises particles in a water dispersant.

Figure 3:
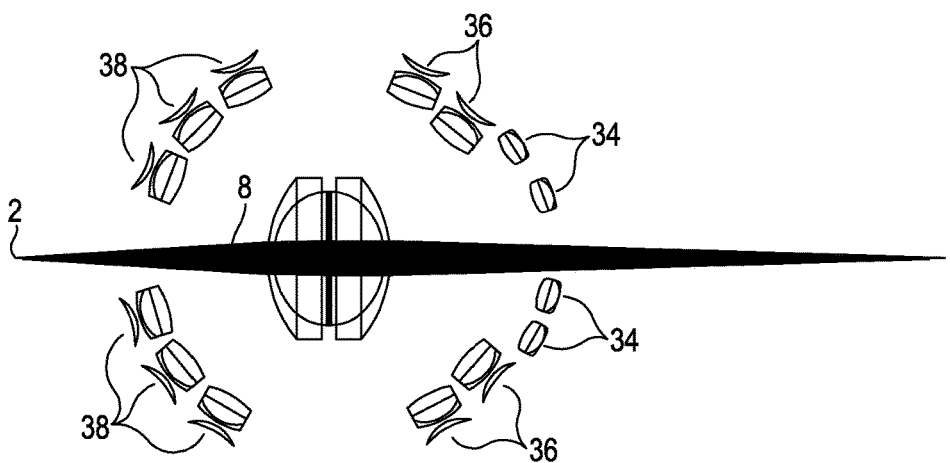
FIG. 3 is a schematic of a light source, sample cell and collection optics for an apparatus according to a first embodiment of the invention.

In FIG. 3, the arrangement of FIG. 2 is again shown, with a plurality of optical collectors 34, 36, 38 for directing light scattered by the sample onto detectors (not shown). Forward scattered light, which leaves the optical cell 30 via the second wall 15 is collected by two different types of collector 34, 36. For low scattering angles, a plurality of single component lens collectors 34 are used, comprising a bonded doublet. For scattering angles or more than around 45 degrees, and for back scattered light (in which the scattering angle is greater than 90 degrees), two component collectors 36, 38 are respectively used, comprising a bonded doublet and a further plano-convex lens. A plurality of the collectors 36 and 38 is provided.

Figure 4:
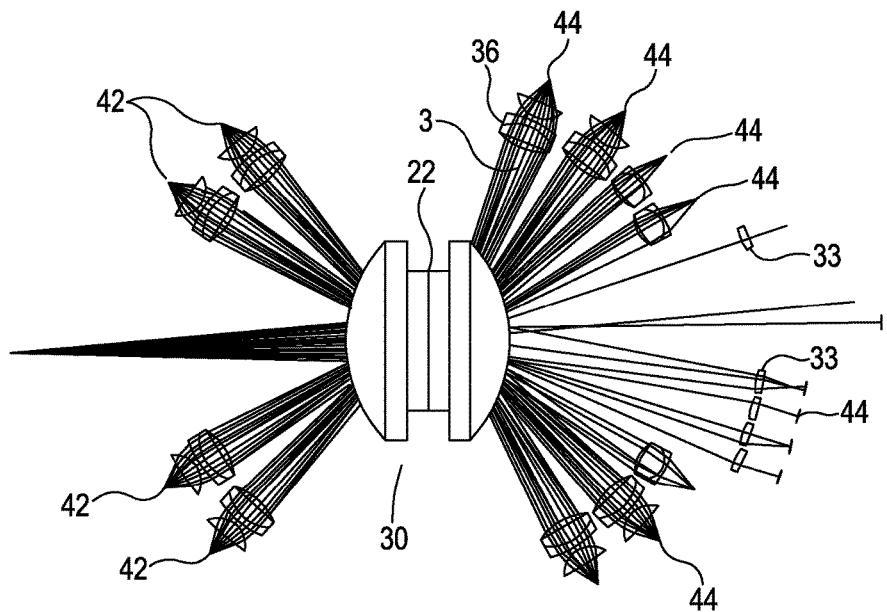
FIG. 4 is ray diagram showing a light beam, and scattered light from the sample for an apparatus according to a second embodiment of the invention.

FIG. 4 shows an alternative arrangement of optical collectors 33, 34, 36, 38, and with associated detectors 44, 42 for detecting forward and backward scattered light respectively. The embodiment of FIG. 4 differs from that of FIG. 3, in that for low angles of scattering of below about 25 degrees, single element collector lenses 33 are used.

Figure 7:
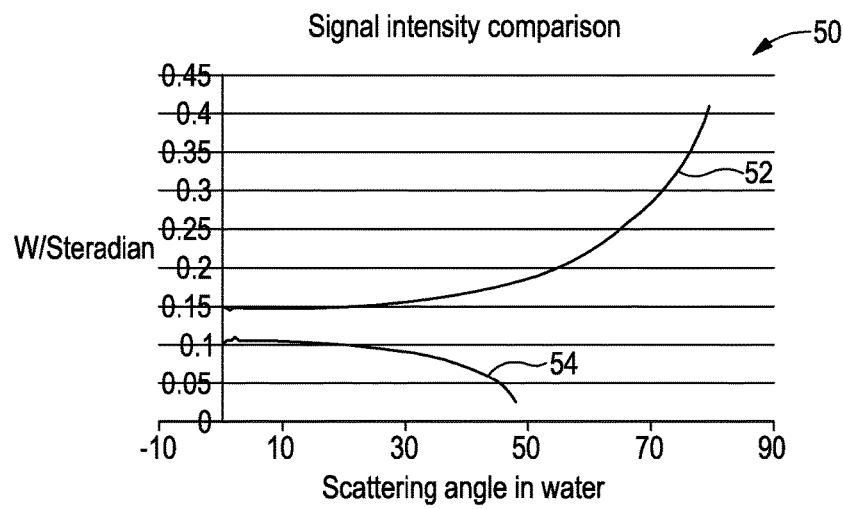
FIG. 7 is a graph comparing signal intensity for a prior art apparatus with an apparatus according to an embodiment of the invention.

FIG. 7 shows a graph 50 of the light intensity in Watts/steradian over a range of scattering angles in a water dispersant from 0 to 90 degrees. A line 52 shows the intensity according to the first embodiment, and a line 54 shows intensity according to the prior art shown in FIG. 1. Both lines are independent of any collection optics. The intensity of light scattered according to the prior art is lower than that according to the first embodiment. In the prior art sample cell, light scattered at angles above the critical angle of 48.6 degrees (for water/air) is totally internally reflected at the external surface of the sample cell. By contrast, the sample cell of the first embodiment has an increasing intensity with scattering angle. The curvature of the external surface of the second wall prevents the reduction of the signal that takes place in the prior art arrangement, in which the light scattered at angles of 0 to 48.6 degrees is spread out over the range of 0 to 90 degrees. Furthermore, in prior art systems the light scattered at angles of more than 48.6 degrees is totally internally reflected and contributes to optical noise. The totally internally reflected light will eventually leave the sample cell as a diffuse haze that will contaminate the rest of the signal.

The increased intensity of scattered light according to embodiments of the invention enables a lower power light source to be used. A lower powered light source is generally smaller, which reduces the overall size of the instrument. This is particularly applicable to systems like the arrangement of FIG. 1, in which a folded optical path is necessary in order to accommodate a relatively large HeNe laser in a relatively compact instrument. The use of a sample cell with comprising a second wall with a curved external surface would allow a HeNe light source of lower power to achieve similar performance, which could subsequently be accommodated with one or no mirrors.

Figure 5:
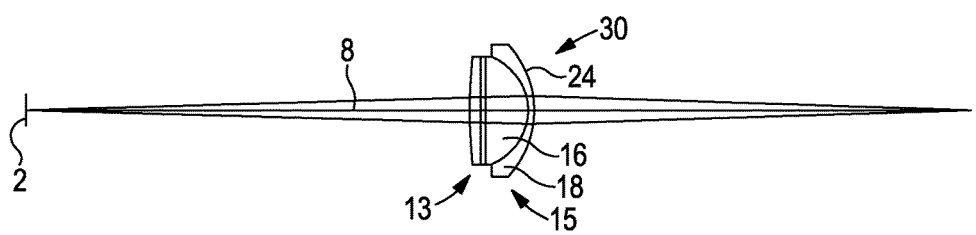
FIG. 5 is a schematic of a light beam path through a sample cell for an apparatus according to a third embodiment of the invention in which the light source has a relatively small numerical aperture.

FIG. 5 shows an embodiment in which the light source comprises a spatially filtered HeNe laser with a relatively low launch numerical aperture. In this embodiment, a relatively low optical power is sufficient to provide the necessary beam quality within the sample 22, and the external surface 26 of first wall 13 of the optical cell 30 accordingly has a larger radius of curvature than the external surface 24 of the second wall 15. The lower optical power of the first wall 13 means that spherical aberration is less critical, and a single plano-convex lens is adequate. The second wall 15 of the sample cell 30 again comprises a doublet lens with a higher optical power than the first wall 13, so as to compensate for refraction at the sample cell/air interface when the dispersant comprises water.

Figure 6:
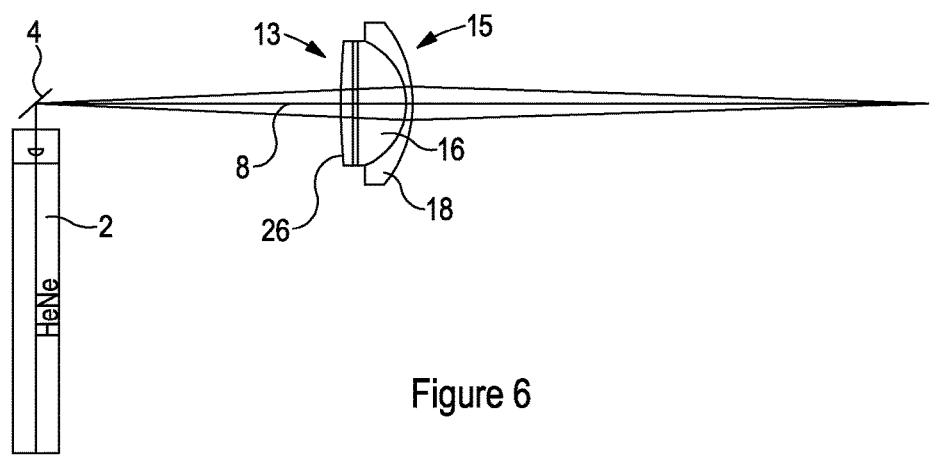
FIG. 6 is a schematic of a light beam path through a sample cell for an apparatus according to a fourth embodiment of the invention in which a single mirror is used to fold the optical path from the light source to the sample cell.

FIG. 6 shows a similar embodiment to that of FIG. 5, but additionally comprising a mirror 4 with a surface at 45 degrees to the beam from the light source 2. The light source 2 therefore launches light at 90 degrees to the axis of the beam through the sample cell, which may allow a more compact design.

Figure 8:
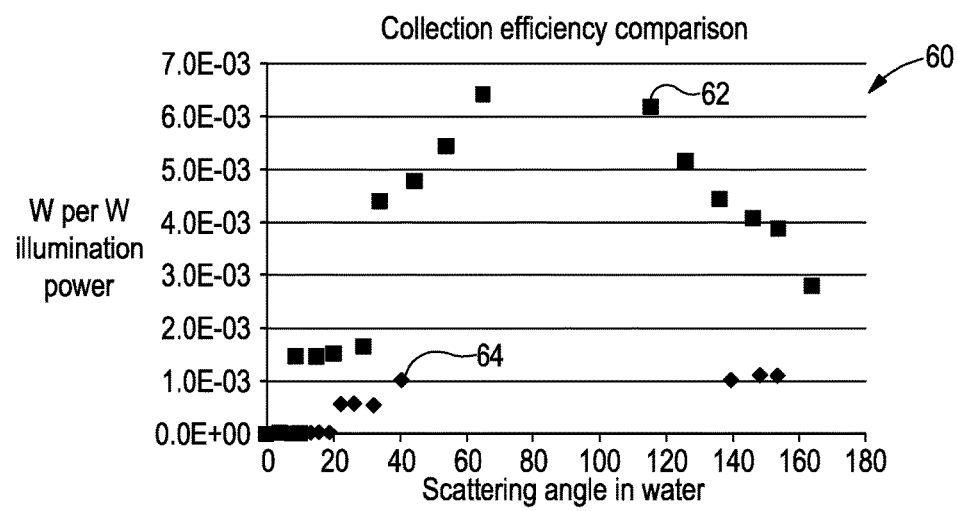
FIG. 8 is a graph comparing collection efficiency for a prior art apparatus with an apparatus according to the first embodiment of the invention.

FIG. 8 is a graph 60 comparing the collection efficiency, in Watts per Watt of illumination power at a range of scattering angles, for the first embodiment, as shown in FIG. 3, and a prior art arrangement based on FIG. 1. The graph includes scattering angles over the full range of 0 to 180 degrees, with a series of points 62 for the embodiment of FIG. 3 and a series of points 64 for the prior art arrangement. The collection efficiency for the embodiment of FIG. 3 is improved at every angle, and the range of angles previously precluded by total internal reflection in the prior art arrangement have a very high collection efficiency in the embodiment of FIG. 3 (of at least 0.004).

Figure 9:
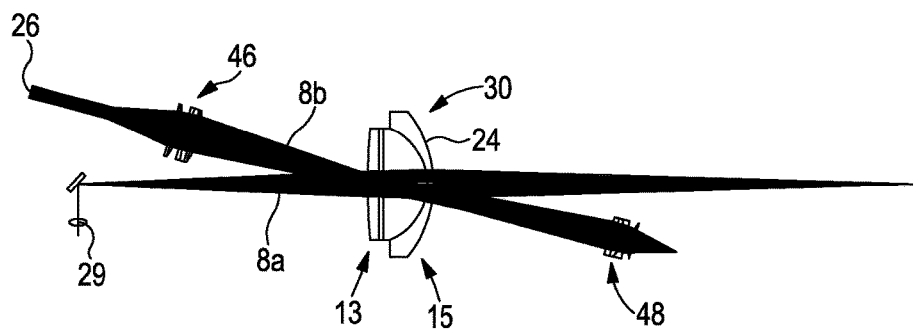
FIG. 9 is a ray diagram of part of a fifth embodiment, showing a sample cell illuminated by a first and second light source.

FIG. 9 shows an embodiment comprising a first light source 2a and a second light source 2b. The first light source 2a comprises a red laser, and the second light source comprises a blue monochromatic light source, such as an LED. The refractive power resulting from the curved external surface 24 of the second wall 15 of the sample cell 30 allows for more intense illumination of the sample by the second light source 2b. The diameter of the illuminated area in the cell is fixed. To increase the amount of light within the illuminated area when using the second light source 2b, the range of angles from which the area is illuminated must be increased. This tends to cause the beam 8b to diverge away from the cell, which would consequently require larger collection optics (to capture the diverging beam). Larger collection optics would be difficult to accommodate while maintaining sufficient angular resolution in detection and a compact instrument.

The refractive power of the second wall 15 of the sample cell 30 reduces the divergence of light leaving the sample cell, helping to keep beam diameters leaving the sample cell low. Analyses comparing achievable illumination intensities using a blue LED as a second light source 2b for prior art sample cells and using a sample cell 30 comprising a second wall with a curved external surface has shown that the intensity of illumination can be increased by a factor of around 2.7 using a sample cell according to an embodiment.

A further problem which is addressed by a sample cell comprising a second wall with a curved external surface is that of crosstalk due to reflection from the external surface of the second wall. Some of the forward scattered light reflects from the interface at the external surface of the second wall. This external surface may be coated with an anti-reflective (AR) coating in order to reduce such reflections. Often, the reflectivity of such AR coatings increases with the angle of exitance.

Figure 10:
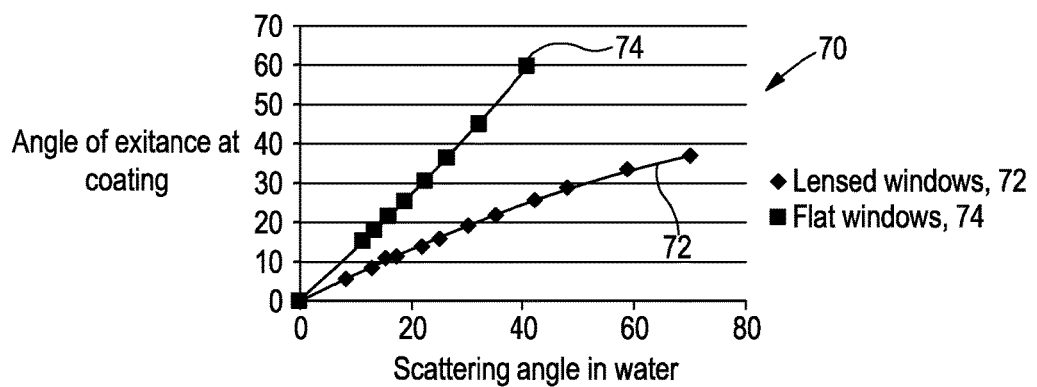
FIG. 10 is a graph comparing an angle of exitance at the external surface with respect to an angle of scatter for a prior art sample cell with that for a sample cell according to the first embodiment of the invention.

FIG. 10 is a graph 70 comparing the angle of exitance over a range of scattering angles in water between a prior art sample cell of FIG. 1 (with flat windows) and a sample cell as shown in FIG. 2. A line 72 shows the angle of exitance for the embodiment of FIG. 2, and a line 74 shows the angle of exitance for the prior art sample cell of FIG. 1. The angle of exitance is lower for the sample cell according to the embodiment of FIG. 2 across the full range of scattering angles. This has the effect of reducing reflections from the external surface of the second wall, thereby reducing crosstalk. Crosstalk tends to reduce the signal to noise ratio.

A sample cell according to an embodiment may be configured to allow light scattered from the sample at relatively high scattering angles to escape from the external surface of the second wall without total internal reflection, when the sample comprises particles in a water dispersant. This enables scattering from bubbles to be differentiated from scattering by particles.

Figure 11:
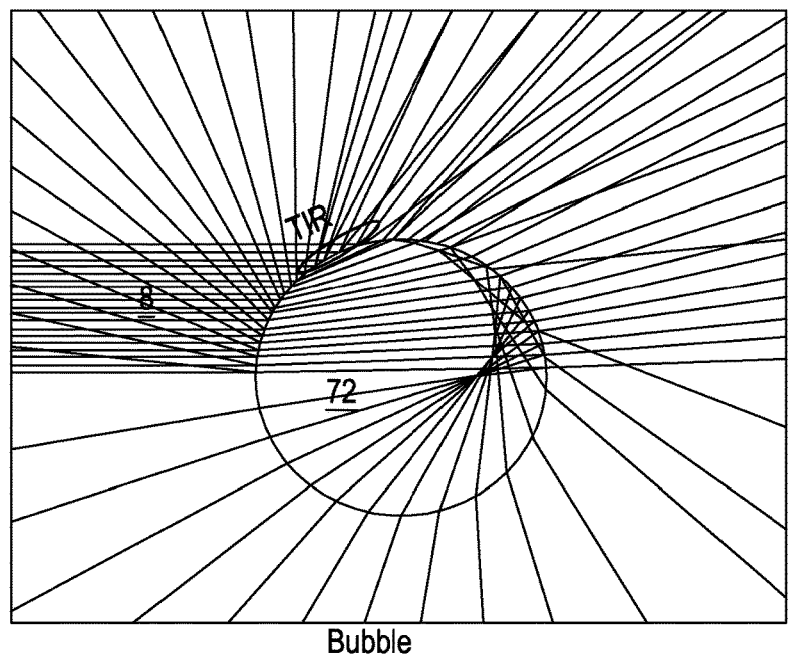
FIG. 11 is a ray diagram showing how a collimated light beam is internally reflected and totally internally reflected from an air bubble in water.

Bubbles scatter light in many directions by internal reflection. Accurate characterisation of low concentrations of relatively large particles may require that bubbles of a similar size can be differentiated from the particles. Bubbles, in contrast to particles of a similar size, scatter light strongly at high angles, due to total internal reflection at the water/air interface of the bubble. This is illustrated in FIG. 11, which shows a collimated light beam 8, incident on a bubble 72. Totally internally reflected light is indicated by TIR.

Figure 12:
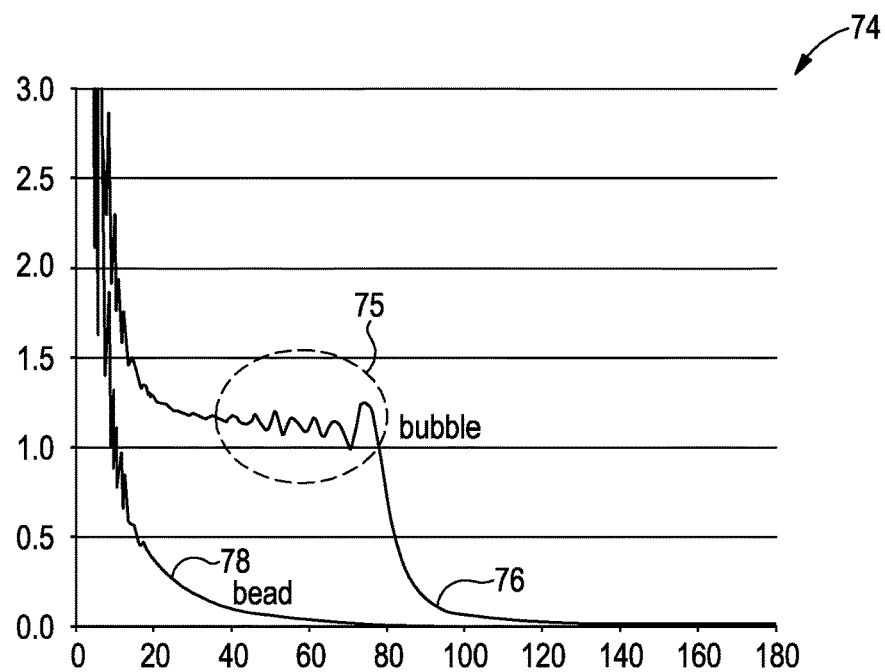
FIG. 12 is a graph showing the relationship between the intensity of scattered light and the scattering angle for a 50 µm glass bead and a 50 µm bubble.

FIG. 12 is a graph 74 comparing the scattering intensity over a range of angles for a bubble 76 and a glass bead 78. The bubble and bead are both 50 μm in diameter. The shape of the scattering curve of the bubble 76 can be differentiated from that of the bead 78 by the strong reflections at angles between 45 and 80 degrees. Light scattered at these angles tends to be lost due to total internal reflection in prior art instruments, but a sample cell comprising a wall with a curved external surface allows light scattered at this range of angles to escape the sample cell and be detected. The light scattered at high angles that characterises scattering from bubbles can be used to differentiate bubbles from particles dispersed in the sample.

For example, there is a marked difference in the ratio of forward scattered light at scattering angles in the range of around 30° to around 80° to back scattered light. One way of distinguishing light scattered by bubbles from light scattered from particles is therefore to determine a ratio of forward scattered light at angles of at least 35° and back scattered light. If the ratio is above a threshold value, the scattered light can be identified as being from bubbles.

Normally, particle characterisation instruments that use scattered light to characterise particles deal with an averaged response from a large number of particles. Scattering from on the order of 1000 particles may be combined to produce the measurement from the instrument. This averaging over a large number of particles tends to mask the detection of large particles. There may be only a few large particles in the sample, but they may have the potential to block or clog the instrument, or to cause a spurious, inaccurate result if they are not detected and the proper action taken.

In order to improve the detection of large particles, individual detectors can be monitored for signals that may indicate a large particle as the measurement is performed (before averaging). When signals are detected that may be indicative of a large particle, the output from the detectors at angles of greater than 35° (or another selected angle) may be analysed to determine whether the signals are indicative of a large particle, or a bubble.

In this way, data from large particles and bubbles can be measured prior to data averaging and analysed separately. This avoids phantom peaks due to bubbles in the large particle size range, and provides cleaner data with less noise for the small sized particles. Furthermore, it allows remedial action to be taken to avoid clogging by large particles, with less potential for false positives due to bubbles (which are not a cause of clogging).

Figure 30:
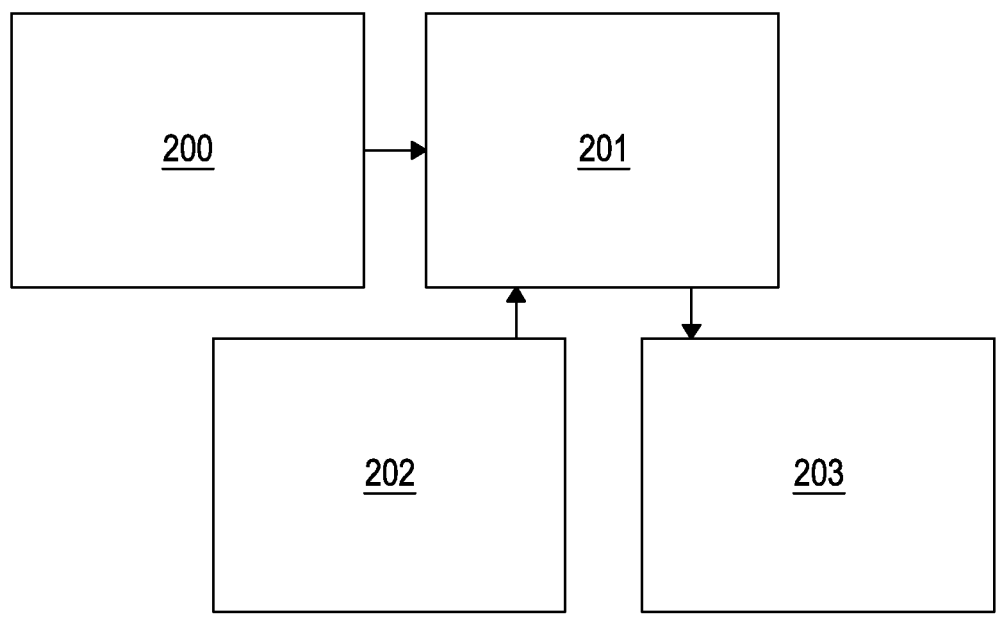
FIG. 30 is a block diagram illustrating a system for bubble detection according to an embodiment of the invention.

FIG. 30 shows a schematic of an instrument configured to distinguish bubbles from particles in a sample. Apparatus 200 is provided, comprising a light source, sample cell and detector, for detecting light scattered from the sample at angles of at least 35 degrees. The output from the detector of apparatus 200 is received by a processor 201, which processes the data and differentiates bubbles from particles by the strong reflections at high scattering angles from bubbles. The processor 201 may subsequently display the results on the display device 203. The instrument may be controlled by the user, via the processor 201, using a suitable input device 202 (such as a keyboard and mouse.

Figure 13:
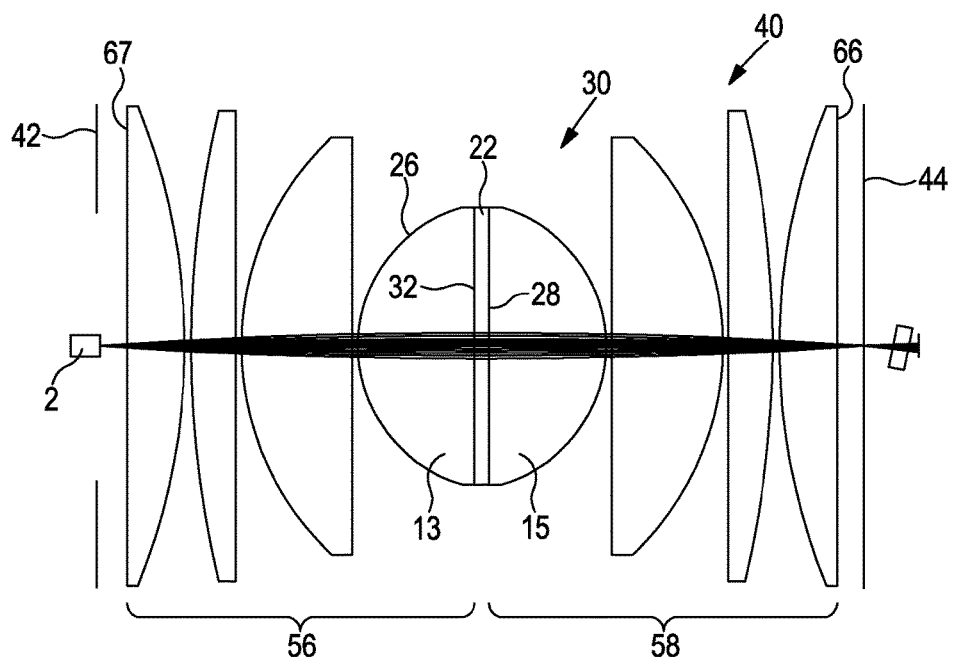
FIG. 13 is a schematic of an apparatus according to a sixth embodiment of the invention, in which a symmetric first and second optical group are employed to direct forward and backscattered light from a broad range of scattering angles to a first and second planar detector arranged to detect forward scattered light and backscattered light respectively.

FIG. 13 shows an apparatus according to a fifth embodiment of the invention, comprising a light source 2, a first optical group 56, a second optical group 58, a first planar detector 44, and a second planar detector 42. A sample cell 30 is provided, which contains a sample 22 that is between the first and second optical group 56, 58. The sample cell 30 comprises a first wall 13 through which a light beam 8 from the light source 2 illuminates the sample, and a second wall 15 through which the light beam 8 exits the sample, absent any scattering. The first wall 13 and second wall 15 are symmetric about the centre of the sample 22, respectively comprise a planar internal surface 32, 28 and a convex external surface 26, 24. The first wall 13 and second wall 15 are therefore both plano-convex lenses. The first optical group 56 therefore comprises the first wall 12 and the second optical group 58 comprises the second wall 15.

The first and second optical group 56, 58 are symmetrical about the centre of the sample 22, and each consists only of plano-convex lens elements (although other types of lens element may be used, as appropriate). In the present embodiment there are four lens elements in each group 56, 58. The lens element of the first and second group 56, 58 that is furthest from the sample each has a respective planar surface 66, 67 facing away from the sample 22. The three lens elements of each group that are closer to the sample each have a planar surface that faces the sample 22.

Figure 14:
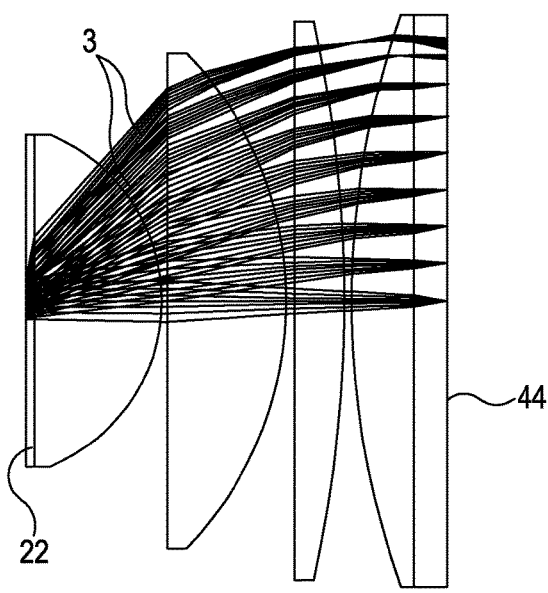
FIG. 14 is a ray diagram showing how forward scattered light is directed by the second optical group onto the first detector, according to the sixth embodiment.

The first planar detector 44 is adjacent with and parallel to the planar surface 66, and thereby detects forward scattered light from the sample 22. FIG. 14 is a ray diagram illustrating the paths of forward scattered light 3 for a range of scattering angles. Light scattered at angles including at least from 5 to 80 degrees are focussed on the planar detector 44, and are incident substantially normal to the plane of the detector 44.

Due to the symmetry of the arrangement (about the sample 22), back scattered light (scattered at a range of angles including at least from 100 degrees to 165 degrees) traces similar paths to the second planar detector 42, which is likewise disposed adjacent with and parallel to the planar surface 67.

The first and second planar detectors 44, 42 each comprise a focal plane array having a plurality of light detectors on a single silicon substrate. In other embodiments, a plurality of detectors or detector arrays may be arranged on a planar carrier. A focal plane array has the advantage of reducing assembly and electrical interconnection requirements for the detector, and may also facilitate a reduced pitch between adjacent detectors. A focal plane array detector may therefore be more suitable for compact devices. A focal plane array has the further advantage of eliminating silicon edges in the focussed light field, which could otherwise result in scattering, giving rise to optical noise.

The second detector 42 comprises an opening. The light source 2 may be disposed in the opening, or may arranged behind the second detector 42, so that the light beam 8 passes through the opening. The first and second planar detectors 44, 42 each have an extent corresponding with that of the respective adjacent planar surface 66, 67. The first and second planar detectors 44, 42 are each configured to capture light scattered over the full range of azimuthal angles. This greatly increases the amount of light captured at each scattering angle.

Using a single optical group 56, 58 and a single detector 44, 42 to collect forward scattered light and back scattered light respectively over a broad range of scattering angles simplifies the instrument. Fewer lens groups and lens elements are required, and less alignment of optical elements is required to build the apparatus. The mounting and electrical interconnections for the plurality of collectors and detectors at different locations and angles for embodiments like that of FIG. 3 is avoided. Furthermore, the alignment that is required is with respect to the common axis of the light beam 8, rather than with respect to a range of different scattering angles. The arrangement is also very compact, making efficient use of volume.

The light source 2 in this embodiment is a 100 mW diode laser, and with a wavelength of 405 nm. Such laser diodes are relatively low cost and compact, and provide a high light output.

This arrangement can be readily scaled, depending on performance requirements. Larger designs are more suitable for characterising larger particles. The embodiment of FIG. 13 is approximately 150 mm long, and around 100 mm wide, and is suitable for characterising particles up to around 65 μm in diameter. The largest optical elements have a radius of around 45 mm.

In the embodiment of FIG. 13, the light beam 8 through the sample 22 is broader than the width of the sample, and the beam 8 is narrow at the first detector 44. The first detector 44 has an opening through which the beam passes to be absorbed by a non-reflecting heat sink 69. The narrow beam 8 at the first detector results in a narrow opening, which may need to be aligned with a high degree of accuracy.

Figure 15:
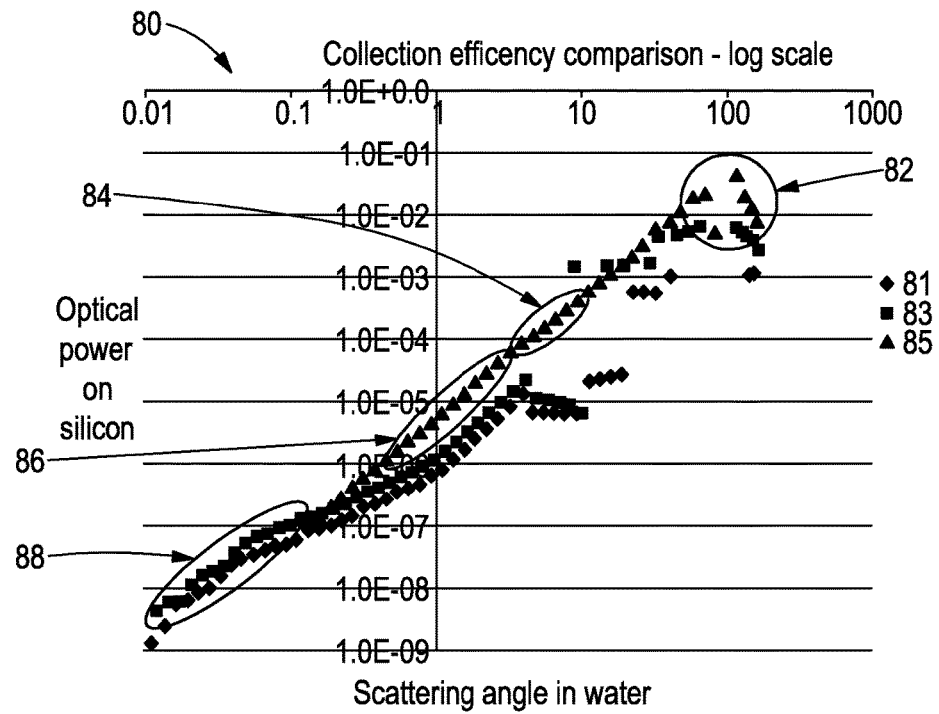
FIG. 15 is graph comparing collection efficiency with respect to scattering angle for: i) a prior art apparatus; ii) an apparatus according to FIG. 3; and iii) an apparatus according to FIG. 13.

FIG. 15 is a graph 80 comparing the collection efficiency for: the embodiment of FIG. 13 (data series 85); the embodiment of FIG. 3 (data series 83); and a prior art arrangement according to FIG. 1 (series 81). At high scattering angles, the performance of the embodiment of FIG. 13 is substantially improved over the other arrangements, as indicated by arrow 82. Collection efficiency is improved by factors of 10-100 at scattering angles of 3-10 degrees, and a factor of 5 improvement is achieved down to angles of around 0.5 degrees. At scattering angles below 0.1 degrees, the collection efficiency of the embodiment of FIG. 13 is reduced over the other arrangements, as indicated by arrow 88. The minimum detectable scattering angle may be limited by the pitch of the detector elements at the first detector array.

Figure 16:
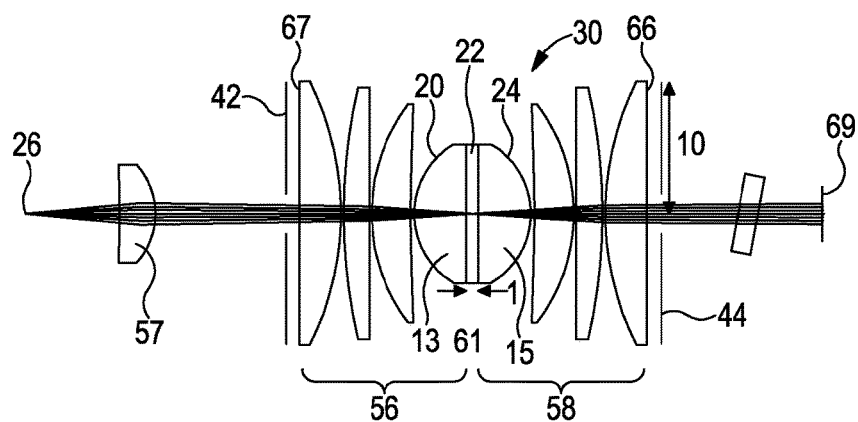
FIG. 16 is a schematic of an apparatus according to a seventh embodiment of the invention, which is a compact configuration that is similar to that of FIG. 13, but which is arranged to focus the light beam through the sample to a narrow beam.

FIG. 16 shows a seventh embodiment of the invention, which is similar to the embodiment of FIG. 14. In this embodiment, the apparatus is even more compact, with a total length (from light source 2b to heat sink 69) being around 61 mm. The radius of the largest optical element is approximately 10 mm, and the width of the sample is around 1 mm.

Figure 17:
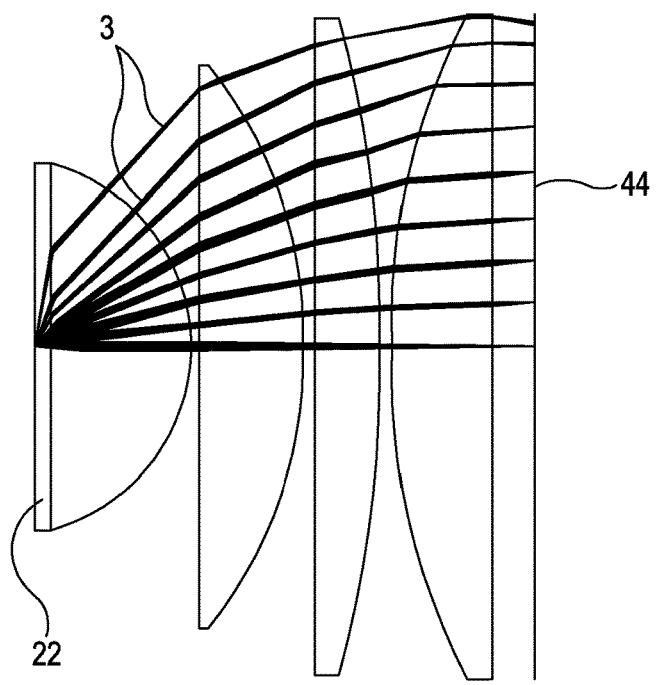
FIG. 17 is a ray diagram showing how forward scattered light is directed by the second optical group onto the first detector, for the apparatus according to FIG. 15.

The light source 2b is again a 405 nm laser diode, having a numerical aperture of 0.09. In this embodiment the light source 2b is behind the second detector 42. A further converging lens 57 is arranged between the light source 2b and the second detector 42. The light beam 8 in this embodiment is a narrow collimated beam within the sample 22, and is broader where it passes through the first and second detectors 44, 42. The $1/e^2$ beam width in the sample 22 is less than 0.5 mm. Similar collection efficiencies are expected for this embodiment as for the fifth embodiment. FIG. 17 illustrates the path of forward scattered light through the second optical group 58 of this embodiment. Light scattered at angles of up to 80 degrees in the sample is again collected and focused normally incident to the detector 44.

The 360 degree azimuthal collection of scattered light is particularly relevant to this embodiment because only a small number of particles may be illuminated by the narrow light beam 8 at any specific time. Instead of averaging out the shape information by sampling many different samples, the averaging may be done by the detectors 44, 42. Each detector 42, 44 could be segmented azimuthally to retain shape information.

The detectors 44, 42 in this embodiment are again focal plane arrays of photodiodes. In smaller arrangements like that of FIG. 15, it may be appropriate to use a rectangular or square focal plane array, with dimensions large enough to capture the full range of scattered light collected by the respective optical groups 58, 56.

Figure 18:
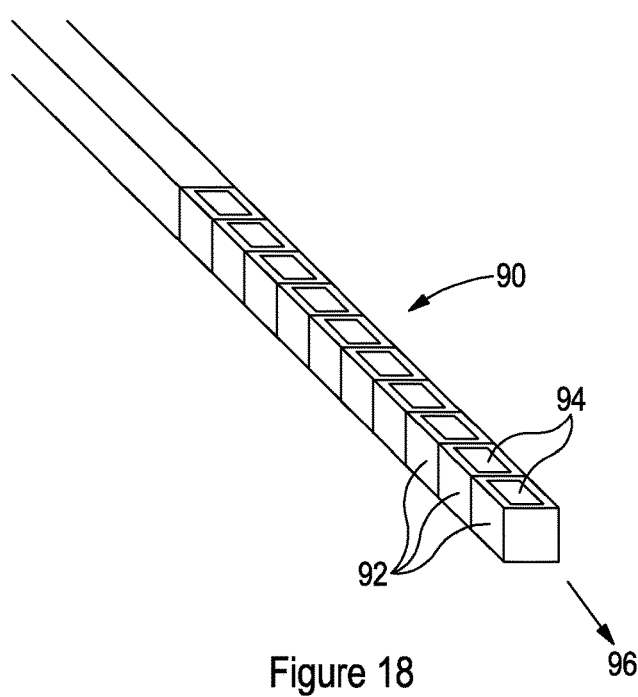
FIG. 18 is a schematic of a plurality of sample holders for transferring a plurality of samples into and out of the sample cell.

The internal volume of the sample cell 30 is relatively small in this embodiment. Medium sample volumes may be continuously flowed through the sample cell 30 during measurement. For very small volumes, the sample 22 may be introduced via an array of small holders 92, as shown in FIG. 18, which may have internal volumes 94 in the microliter range. The array of sample holders 92 could be translated into the beam 8 one by one, in the direction indicated by arrow 96, to allow a plurality of samples to be characterised in sequence.

Where such an array of sample holders is used with a sample cell comprising a curved external surface, as in the sixth embodiment, there should not be an air gap between the buckets and the cell window, otherwise total internal reflection may occur at the interface. One way of avoiding an air gap is to arrange a fluid such as water in the sample cell 30 to fill the gap between the sample holders 92 and the internal wall of the sample cell.

Figure 19:
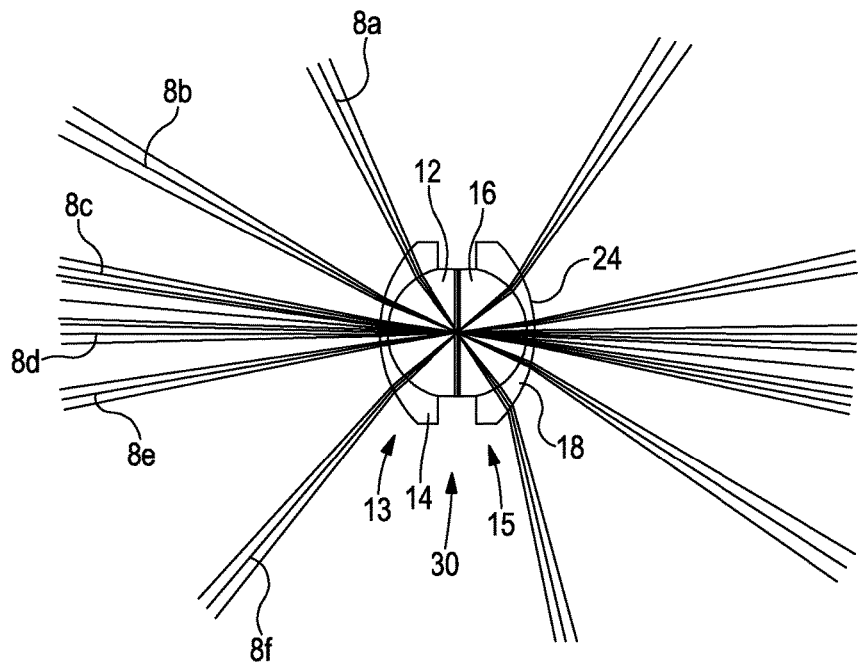
FIG. 19 is a ray diagram showing a sample cell according to the first embodiment being illuminated along a plurality of optical paths by a plurality of separate light beams, the different light beams being suitable for carrying out a number of different optical analyses.
Figure 20:
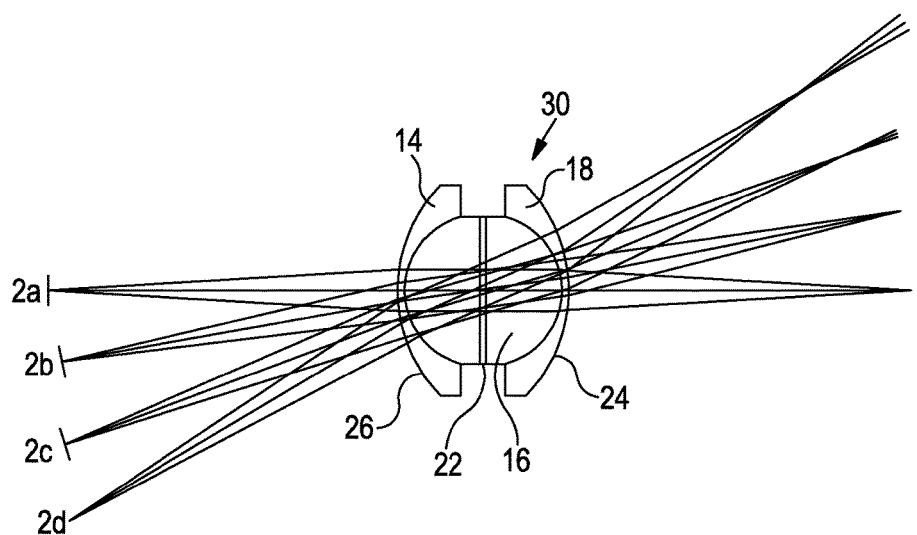
FIG. 20 is a ray diagram showing four overlapping light beams illuminating a sample cell according to a first embodiment, so as to perform a plurality of different measurement techniques.

FIG. 19 illustrates that in some embodiments, a plurality of light sources may be provided for carrying out different experiments on a sample. This may be particularly applicable to an arrangement in which the sample is small, and/or arrangements which incorporate a plurality of moveable sample holders arranged to allow measurements to be carried out on each small sample. The use of a sample cell with a curved external surface 26, 24 on both walls 13, 15 provides a large range of angles for probe and collection light beams in both elevation and azimuth, as indicated by the non-overlapping beams 8a, 8b, 8c, 8d, 8e and 8f. There are no corners to be avoided on the external surfaces 26, 24, and the walls 13, 15 can provide useful lens power. FIG. 20 illustrates that multiple illumination beams from light sources 2a, 2b, 2c and 2d may overlap at the sample cell 30.

The type of arrangement shown in FIG. 13 enables a compact arrangement in which a single detector be used for detecting light scattered at a large range of angles, and is less sensitive to alignment problems that can cause difficulties in instruments where a plurality of separate detectors and associated lenses are used to respectively detect light scattered at different ranges of scattering angle. There are still some problems with this arrangement though. Firstly, relatively large area detectors 44, 42 are needed to detect forward and backscattered light over a large range of scattering angles. Large area detectors tend to be expensive, and suffer from increased noise due to their increased capacitance. Furthermore, the number of lens elements on the axis of the light source is relatively high. The vast majority of the light will pass straight through the sample without scattering, and the un-scattered light beam 8 will tend to reflect from from each surfaces it enters. Although the proportion of light reflected at each surface is low, the combined effect of the reflected light increases the optical noise in the system.

Figure 21:
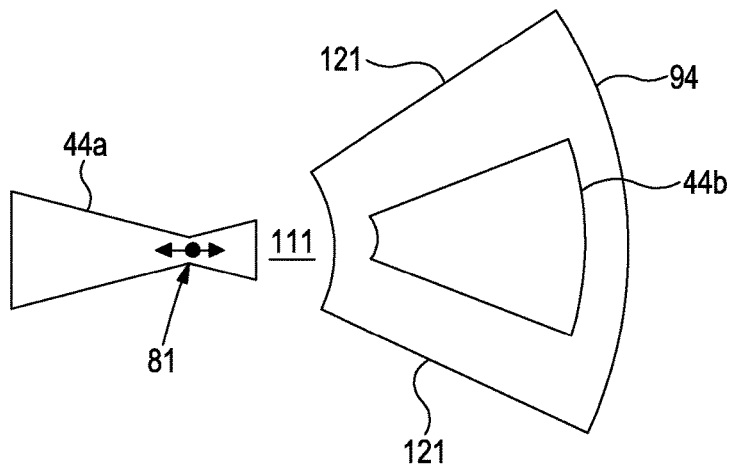
FIG. 21 is a view along a light beam axis of a first and second detector and an associated collecting lens element.
Figure 22:
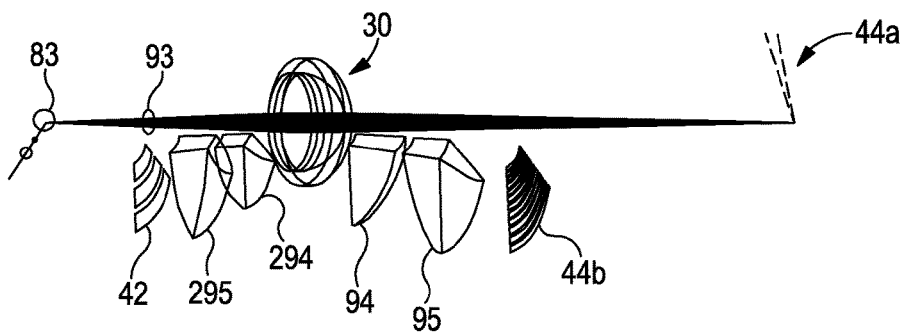
FIG. 22 is a ray diagram of a particle characterisation apparatus according to an eighth embodiment of the invention.

An alternative arrangement that addresses a number of these problems is shown in FIGS. 21 and 22. A pair of collecting lens elements 94 are provided to collect and focus light scattered at a range of angles on the detector 44b. The collecting lens elements 94 and 95 are substantially sector shaped, and are arranged with an open region 111 so that the illuminating light beam can pass through the collecting lens elements 94, 95 without reflecting therefrom. The axis of lens elements 94, 95 may thereby be substantially co-incident with the light beam axis 81 without the light beam reflecting from the lens elements 94, 95.

In this example embodiment there is provided another detector 44a. The detector 44a is for detecting light scattered at a first range of angles to the light beam axis 81 and the detector 44b is for detecting light scattered at a second range of angles to the light beam axis 81. The first detector 44a is arranged to detect light scattered at relatively low angles, and the second detector 44b is arranged to detect light scattered at relatively large angles. The first range of angles includes a lower minimum scattering angle than the second range of angles. The second range of angles includes a larger maximum scattering angle than the first range of angles. There is preferably some overlap between the first and second range of angles.

In the example of FIG. 21, the light beam 8 is plane polarised, and both of the detectors 44a 44b are arranged to capture P-polarised scattered light. The first detector 44a extends away from the light beam axis 81 in the plane of polarisation in a first direction and a second opposite direction, extending further in the first direction than the second. The second detector 44b is offset from the light beam axis 81 in the second direction, and extends away from the light beam axis 81 in the second direction.

Both detectors are preferably substantially wedge or segment shaped, with the centre of the circumferential extent of each detector substantially co-incident with the plane in which the light is polarised. The plane of both the first and second detectors 44a, 44b is substantially normal to the light beam axis.

Figure 29:
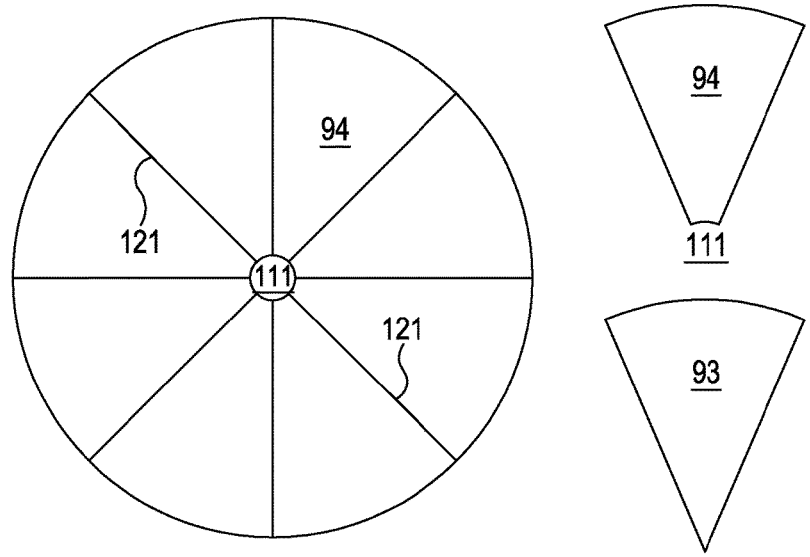
FIG. 29 is a schematic of segment shaped lenses, showing how a circular lens can be cut to form a plurality of segment shaped lenses.

Segment shaped lens elements 94, 93 are more clearly depicted in FIG. 29. FIG. 29 shows how a circular lens element 120 can be divided into a plurality of segment shaped lens elements 94, 93. The circular lens element 120 may first be shaped and polished, and then cut to produce segment shaped elements 94. The circular lens element 120 is preferably cut along radii or diameters 121.

The lens element 93, for instance, may be semi-circular, enabling two such lens elements 93 to be produced from a single blank. Alternatively, the angle subtended by each lens element may be smaller, enabling more lens elements to be produced from a single circular blank. The circumferential angle subtended by the lens element 94, 93 may be divisible into 360°, so that multiple lenses may be cut from a circular blank without waste. The angle subtended by the lens element 94, 93 may be selected from the group of: 10°, 12°, 15°, 18°, 20°, 24°, 30°, 36°, 40°, 45°, 60°, 72°, 90° and 180°.

Optionally, a hollow central core 111 may be formed in the circular lens element 120 before it is divided into segments, so that light on the axis of the lens can bypass it without reflecting therefrom. Segment shaped lens element 93 omits this hollow core 111.

FIG. 22 shows an example embodiment in which segment shaped lenses 94, 95, 294, 295 are used. In this example, each of the segment shaped lens elements 94, 95, 294, 295 also comprise an open region 111 arranged to allow the light beam 8 to pass through the lens element 94, 95, 294, 295 along the axis thereof without reflection. A light beam 8 illuminates a sample cell 30, via a reflector 83. A diverging lens 93 is provided between the reflector 83 and the sample cell 30, to increase the area illuminated within the sample cell 30 by the light beam 8.

The sample cell 30 is according to an embodiment of the invention, having a first and second wall that have respective convex external surfaces. The first wall of the sample cell 30 is arranged to collimate the light beam 8 in the sample. The second wall of the sample cell 30 is arranged to collect and focus forward light scattered at a first range of scattering angles onto a first detector 44a. The first range of scattering angles covers a low range of scattering angles, for example from 0.01° to 20°.

The pair of lens elements 94, 95 are arranged to collect and focus forward scattered light at a second range of scattering angles (for example from 15° to 80°) onto a second detector 44b. Each of the lens elements 94, 95 is preferably segment shaped, and is configured with an open region to allow the light beam to pass through the axis of each lens 94, 95 without reflecting therefrom.

A further pair of lens elements 294, 295 are arranged to collect and focus back scattered light at a third range of scattering angles (for example from 110° to 165°) onto a third detector 42. Each of the lens elements 294, 295 is preferably segment shaped, and is configured with an open region to allow the light beam to pass through the axis of each lens 94, 95 without reflecting therefrom.

Each of the detectors 42, 44a, 44b, is arranged facing normal to the light beam 8, and each of the lens elements 94, 95, 294, 295 is arranged with their axis substantially co-incident with the light beam axis. This arrangement means that it is more straightforward to optically align the components of the apparatus, because they are each referenced to the same datum: that of the light beam axis. This is in contrast to arrangements like that shown in FIG. 4, which requires alignment of a large number of lens elements and detectors in positions that are off-axis.

Figure 23:
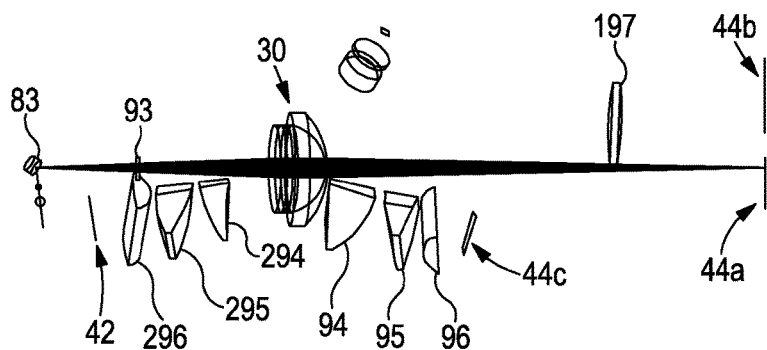
FIG. 23 is a ray diagram of a particle characterisation apparatus according to a ninth embodiment of the invention.

An alternative arrangement is shown in FIG. 23, wherein a first, second, third and fourth detector 44a, 44b, 44c, 44d are arranged to detect forward scattered light at various ranges of scattering angle, and a fourth detector 42 is arranged to detect back scattered light. In this arrangement, further cylindrical lenses 197, 96, 296 are used to focus light at detectors 44b, 44c, 42 respectively, so as to reduce the size of these detectors. In this embodiment detectors 44c, 44d and 42 are not substantially normal to the light beam axis. A normal direction from each of these detectors is instead inclined relative to the light beam axis.

The first forward scatter detector 44a is arranged at the focal distance of the second wall of the sample cell 30, to detect light scattered at a first, low range of scattering angles (for instance from 0.013° to 4.5°). The second forward scatter detector 44b is arranged to detect light scattered at a second, higher, range of scattering angles (for instance from 6° to 13°). The cylindrical lens element 197 is positioned between the second wall of the sample cell 30 and the second detector 44b.

The third detector 44c is arranged to detect forward scattered light scattered at a third range of scattering angles (for instance 33° to 62°), which is higher than the second angular range. Collecting lens elements 94, 95 are configured similarly to the corresponding lens elements 94, 95 in the embodiment of FIG. 22. A further cylindrical lens element 96 is provided between lens element 95 and the third detector 44c, which enables the use of a third 44c detector with a reduced size.

The fourth detector 44d is positioned to detect forward scattered light scattered at angles near to 62° to the light beam axis. A group of conventional circular lens elements 198 are positioned between the fourth detector 44d and the sample cell 30 to collect scattered light and focus it onto the detector 44d.

Lens elements 294, 295, 296 are arranged to collect and focus back scattered light at a range of back scattering angles (for instance at scattering angles of between 140° and) 160° onto the detector 42. A cylindrical lens element 296 is employed between the detector 42 and the other two lens elements 294, 295. Lens elements 294, 295 are configured similarly to the corresponding elements 294, 295 in the embodiment of FIG. 22.

The arrangement of FIG. 23 is relatively complicated, and has a gap in detection angles in the range 14° to 32°. A further detector and associated collecting and focussing optic may be provided to address this (not shown).

Figure 24:
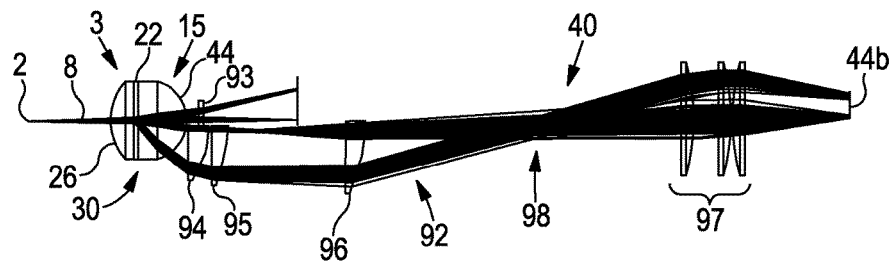
FIG. 24 is a ray diagram of a particle characterisation apparatus according to an tenth embodiment of the invention.

FIG. 24 shows an alternative embodiment, in which a relay lens group 97 is used to extend the optical path, and thereby simplify the collection optics and reduce the total detector area needed for detecting a wide range of scattering angles.

A light source 2 provides a light beam 8 along a light beam axis. A lensed sample cell 30 is provided, having a first wall 13 through which the light beam 8 illuminates the sample 22 and second wall 15 through which the light beam 8 exits the sample cell 30. The external surface 24, 26 of each of the first and second wall 13, 15 through which the light beam 8 passes are convex. The external surface 26 of the first wall 13 has a larger radius of curvature than the external surface 24 of the second wall 15. Both the first and second wall 13, 15 are lenses (for instance, doublet lenses) with a positive optical power, and the second wall or lens 15 has a higher optical power than the first 13. The use of a lensed sample cell 30 is advantageous for the same reasons previously discussed, but it will be appreciated that this is not essential. In some embodiments a flat windowed cell may be used, or a sample cell with a convex external surface on only the first wall 13, or only the second wall 15 may be used.

A split optical path arrangement is used, in which a first optical path 91 is provided for detecting light that is scattered at a first range of angles (for example from 0.1° to) 10°, and a second optical path 92 is provided for detecting light that is scattered at a second range of angles (for example from 8° to 80°). The first range of angles preferably comprises a smaller maximum angle than the second range of angles. Preferably there is some overlap in the first and second range of angles, but in some embodiments the second range of angles does not include angles within the first range of angles.

The use of two optical paths allows for improved performance optimisation, by enabling separate optimisation for both small angle and large angle scattering paths. It will be appreciated that these requirements are in tension if a single optical path is used, because designing to accommodate a large scattering angle tends to have a deleterious effect on the minimum resolvable scattering angle. Although two optical paths are preferable, in some embodiments a single optical path may be used, corresponding with either the first optical path or the second optical path.

Both optical paths 91, 92 are configured for collecting and detecting mainly P-polarised scattered light. The incident light is plane polarised, and P-polarised scattered light is therefore scattered in a direction parallel with the polarisation plane. Each optical path may alternatively be configured to detect light over any azimuthal range (for example over a 360 degree azimuth).

The first optical path 91 comprises a diverging lens 93, which directs light onto the first detector 44a. The first detector 44a is an planar array of photodiodes (e.g. an array of annular photodiodes), and is substantially normal to the axis of the light beam 8. The first detector 44a extends away from the axis of the light beam 8 far enough to detect light scattered at the end of the scattering angle range of the first optical path (for example 10°). The diverging lens increases the angular separation between light scattered at different angles, improving the ability of the instrument to detect and characterise scattering of light at very small angles, thereby improving the ability of the apparatus to characterise relatively large particles. In some embodiments the diverging lens is not used (for example, where characterising larger particles is less emphasised). The first detector 44a may be provided with a hole to allow the un-scattered light beam 8 to pass through the detector array to a light absorbing heat sink.

The second optical path 92 comprises an optical group. The optical group comprises a first group of three lenses 94, 95, 96 and a second relay group of lenses 97, comprising three further lens elements. The lenses 94, 95, 96, 97 of the optical group on the second optical path 92 collect and focus light scattered at a larger range of angles than the first optical path 91, and at higher angles (for example from 8° to 80°). There is an optical inversion point 98 between the first and second group of lenses, at which a mirror may optionally be positioned to fold the optical path so as to reduce the length of the apparatus. The scattered light is directed and focussed by the optical group of the second optical path 92 onto the second detector 44b. The second detector 44b is a planar array of detector elements, is oriented substantially normal to the axis of the light beam 8, and extends away from the axis of the light beam 8. The lenses 94, 95, 96, 97 of the optical group are configured to map scattering angle at the sample 22 to a location or detector element on the second detector array 44b. The distance from the light beam axis on the detector 44b corresponds with the scattering angle, with each scattering angle mapping to a narrow range of distances from the light beam axis.

Each of the lens elements 94-96 are substantially sector shaped when viewed along the axis of the lens element, having a substantially circular edge between two substantially radial straight sides. Although this is advantageous, it will be understood that this is not essential, and arrangements are envisaged in which the lens elements of the second optical path 92 are circular (for instance in an arrangement without the first optical path 91).

Each of the lenses in the embodiment of FIG. 24 are spherical lenses, which are relatively low cost.

An open core 111 may be provided, for allowing the illuminating light beam 8 to bypass the lens elements 94, 95 without interacting therewith. Lens elements 94 and 95 in the embodiment of FIG. 21 preferably have such an open core 111 (although it is not essential). The lens elements 94 and 95 may thereby each be positioned with their axis co-incident with the axis of the light beam 8, so that the un-scattered light beam 8 will pass through the open core 111, without being reflected from the lens 94, 95. This substantially reduces the optical noise that would otherwise result from reflections at the surface of these lenses. A light absorbing heat sink (not shown) is provided to absorb the un-scattered light beam 8.

This design overcomes a number of the problems associated with designs like those of FIG. 13. It has relatively compact detectors 44a, 44b, and greatly reduced stray light as a result of reflections of the light beam 8 at the surfaces of the lens elements. Furthermore, each of the detectors 44a 44b are oriented normal to the light beam axis, and each of the lens elements 93-97 are arranged with their respective axis co-incident with the light beam axis, which simplifies alignment and construction. However, the approach of the embodiment of FIG. 21 is relatively difficult to miniaturise while still achieving good performance at the detector, in which light scattered at a single angle results in a small spot (ideally a point) at the detector.

Figure 25:
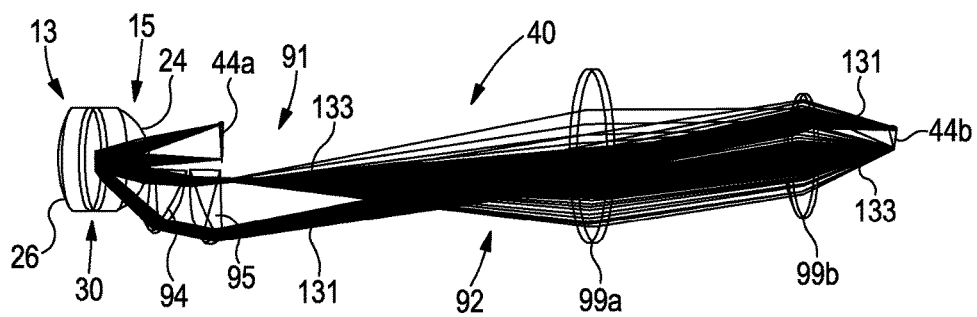
FIG. 25 is a ray diagram of a particle characterisation apparatus according to a eleventh embodiment of the invention.

FIG. 25 shows an alternative embodiment, in which a number of the lens elements in the optical group in the second optical path comprise aspheric surfaces.

In the embodiment of FIG. 25 the second optical path 92 has been optimised for minimising the radial extent of a spot (or point spread function) on the detector 44b, which leaving the tangential extent unconstrained, thereby allowing optical designs that produce a spot on the detector with a relatively large tangential extent. This is advantageous, because it results in a more compact design than would be the case if the optical design were optimised for both tangential and radial spot size. Although advantageous, this feature is not essential, and a working design can be realised while optimising for minimal spot size in both tangential and radial extent.

Figure 32:
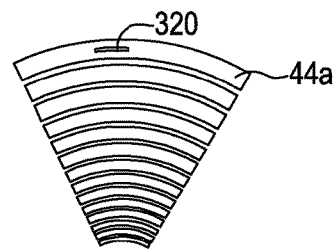
FIG. 32 is a detector showing an arc shaped point spread function of the collection optics at the detector.

FIG. 32 illustrates an arc shaped point spread function of a collection lens (or lens group) at a detector 44a. The detector comprises an array of arc shaped detector elements. Optimising for a narrow point spread function at the detector in a radial direction only tends to result in broader, arc shaped point spread function in the tangential direction. In this example, the tangential extent of the point spread function at the detector 44a is at least a factor of 2 greater than the radial extent thereof, and the factor may as great as 3, 4, 5, 10, 50 or 100.

Figure 28:
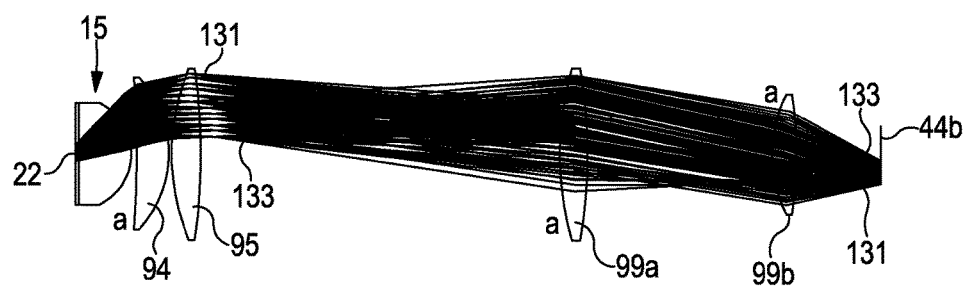
FIG. 28 is a ray diagram showing the second optical path of the twelfth embodiment of the invention.

A design for the second optical path 92 is also shown in FIG. 28, in which the lenses 94, 95 are shown as circular. It will be understood that the optical design is the same, whether these elements 94, 95 are circular or segment shaped. Aspheric surfaces a are clearly shown in FIG. 28. The first aspheric surface a is the surface of lens element 94 that faces the sample 22. The second aspheric surface a is the surface of lens element 99a that faces the sample 22. The third aspheric surface a is the surface of the lens element 99b that faces the sample. In other embodiments, different surfaces may be aspheric. This design has been found to result in aspheric surfaces that are reasonably close to spherical, which may be more straightforward to manufacture.

The use of aspheric surfaces and lack of constraint in tangential spot size both contribute to realising a relatively compact design that performs well at a wide range of scattering angles, and which is less sensitive to misalignment errors than prior art instruments which use a plurality of angled individual detectors to detect light scattered at different angular ranges. The continuous light field, covering a relatively broad range of angles, at each of the first and second detector 44a, 44b means that problems that result from misalignment of collection optics and/or detectors is mitigated. If a misalignment occurs, there is less chance of the light field falling off the edge of the detector with an arrangement where a substantially continuous light field corresponding with a broad range of scattering angles is available at the detector 44b. Furthermore, it is more straightforward to compensate for any misalignment of the sensor element 44a, 44b according to embodiments of the present invention.

Figure 27:
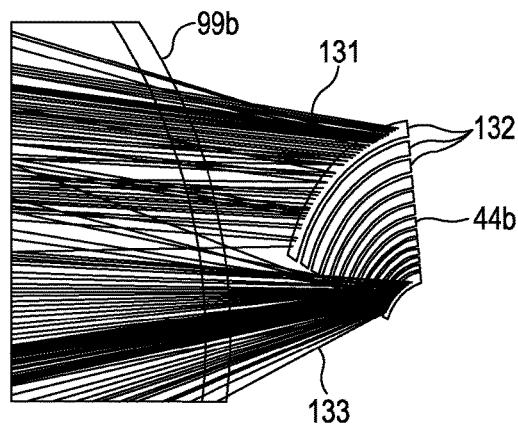
FIG. 27 is a ray diagram showing rays converging on a detector in the twelfth embodiment of the invention.

Lens elements 94, 95 are again preferably segment shaped, with hollow cores 111 to allow the light beam 8 to bypass them without contributing to stray light by reflecting therefrom. The final two collecting lenses 99a, 99b are circular spherical lenses, which focus the light onto the detector 44b. The second detector 44b is again a planar segment shaped array of detector elements, oriented normal to the axis of the light beam 8 and extending away from the light beam axis. The relatively broad spot size at the second detector 44b in the tangential direction means that each detector element 132 of the second detector 44b may be somewhat larger in azimuthal extent than each detector element of the first detector 44a. This is more clearly shown in FIG. 27, which illustrates light scattered at a small range of relatively large angles 131 and light scattered at a small range of relatively small angles 133, each respectively focussed on a different annular detector sub-element 132.

The first optical path 91 in the embodiment of FIG. 25 omits the diverging lens 93 that was used in the embodiment of FIG. 24, which results in a more compact first detector 44a, and a slight reduction in the size of the largest particles that can be characterised. Omitting the diverging lens 93 may reduce stray light that results from illuminating light beam 8 reflecting from the diverging lens 93, and decreases the number of lens elements, which may reduce cost.

Figure 26:
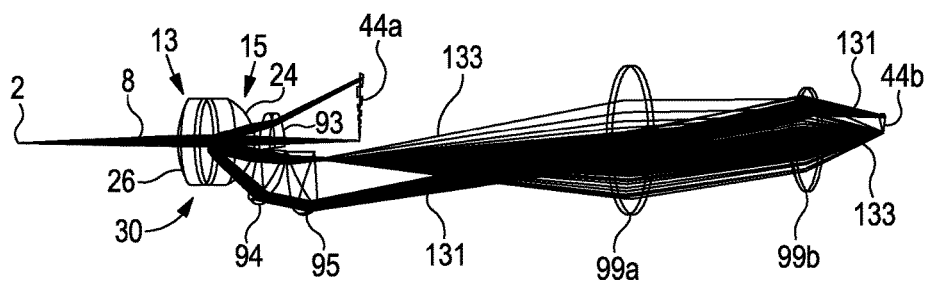
FIG. 26 is a ray diagram of a particle characterisation apparatus according to a twelfth embodiment of the invention.

FIG. 26 shows a similar arrangement to that of FIG. 25, but includes a diverging lens 93 in the first optical path 91, resulting in improved performance in characterising larger particles, but requiring a larger first detector 44a. The second optical path 92 in this embodiment is substantially identical to that used in FIG. 25.

In each of the embodiments of FIGS. 24-26, a further detector may be included, to detect backscattered light from the sample 22. The performance of the apparatus in detecting backscattered light may be less critical than for forward scattered light, and a more conventional arrangement for detecting backscattered light, similar to that shown in FIG. 4 may be used. Alternatively, an arrangement similar to that of the second optical path 92 for forward scattered light of any of FIGS. 24-26 may be used for detection of backscattered light.

A further collection lens and a third detector (not shown) may be provided for detecting back scattered light from the sample 22. This arrangement may comprise a detector that is at an angle with respect to the axis of the light beam 8. The back scatter detector may be positioned remote from the axis of the light beam 8. The backscatter detector may be configured to collect only a limited range of scattering angles near to the axis of the light beam 8 so as to minimise cross talk from reflections at the water-lens boundary within the sample cell 30 (when the sample is dispersed in water), because there is little spatial information in the higher back-scattered angles anyway. For very small sized particle characterisation, only a relatively small range of back scattering angles (for example at a range of around 120°-150° to the light beam axis) may be collected in backscatter. The backscatter detector (and any associated lens elements or optics) may be placed away from light reflected from segment shaped lenses, for example at different azimuthal angle.

Figure 31:
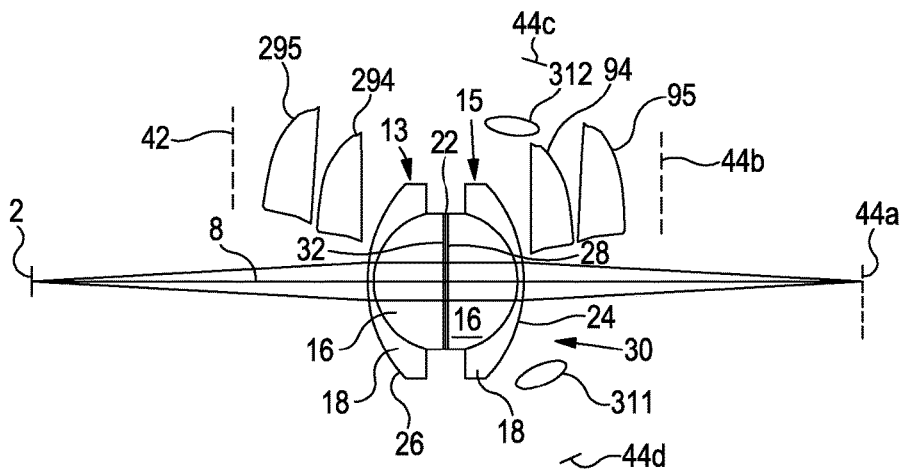
FIG. 31 is a schematic diagram of a particle characterisation apparatus according to an embodiment of the invention.

FIG. 31 shows an embodiment of the invention comprising a light source 2, sample cell 30, first, second, third and fourth forward scattered light detectors 44a-d, and back scattered light detector 42. The light source 2 illuminates the sample cell 30 with a light beam 8.

The sample cell 30 comprises a first wall 13, through which the light beam 8 illuminates the sample 22, and a second wall 15 through which the light beam 8 exits the cell 30 after it has illuminated the sample 22. The first wall 13 and second wall 15 comprise doublet lenses, each lens having a convex external wall and planar internal wall. The planar internal walls are parallel, and define a volume within which the sample 22 is located. The sample cell 30 is symmetric about a central plane which is equidistant from the planar internal walls of the first and second cell walls 13, 15.

Forward scattered light resulting from the interaction of the light beam 8 and the sample 22 leaves the cell 30 via the second cell wall 15. Light scattered at a first range of angles (for instance 0.01-5 degrees) is focussed by the second wall 15 of the sample cell 30 onto the detector 44a. Light scattered at a second range of angles comprising larger angles than the first range of angles (for instance, 6-70 degrees) is collected and focussed by lenses 94, 95 onto detector 44b. The third detector 44c is arranged to detect light scattered at a third range of angles that comprises angles greater than those of the second range. The third range of angles is narrower than the second range. A lens 312 is provided to collect and focus light on the third detector 44c. The fourth detector 44d is arranged to detect light scattered at an angle that is within the second range of angles, and a lens 311 is provided to collect and focus light onto the fourth detector 44d.

In the back scatter direction, detector 42 and lenses 294 and 295 are arranged to collect and focus back scattered light on the back scatter detector 42. In some embodiments the back scatter detector 42 and lenses 294 and 295 correspond with detector 44b and lenses 94, 95, mirrored about the central plane of the sample 22.

Detectors 44a, 44b and 42 are focal plane array detectors, which preferably comprise a one-dimensional array of annular light detector elements. Each of lenses 94, 95, 294, 295 are sector shaped lenses, and comprise an open region co-incident with their axes through which the light beam 8 passes. Each of the lenses 94, 94, 294, 295 is arranged with its optical axis substantially coincident with the light beam axis 8. Each of the detectors 44a, 44b and 42 have a plane that is substantially normal to the light beam axis. Detector 44a is at a larger distance from the sample cell than detector 44b.

Detectors 44c and 44d are more conventional, being arranged at an angle to the light beam axis corresponding with the range of scattering angles that the detectors 44c, 44d are arranged to detect. Similarly, the collection lenses 311, 312 for these lenses are each oriented with their lens axis parallel to the direction that the scattered light they are to collect exits the sample cell 30.

The embodiment of FIG. 31 can be thought of as a hybrid approach, that is between the more conventional detector arrangement of FIGS. 3 and 4 in which angled detectors with corresponding angled collection optics are used, and arrangements like that of FIG. 22, in which all of the detectors are focal plane arrays, and each of the detectors is oriented with its plane substantially normal to the light beam 8.

Figure 33:
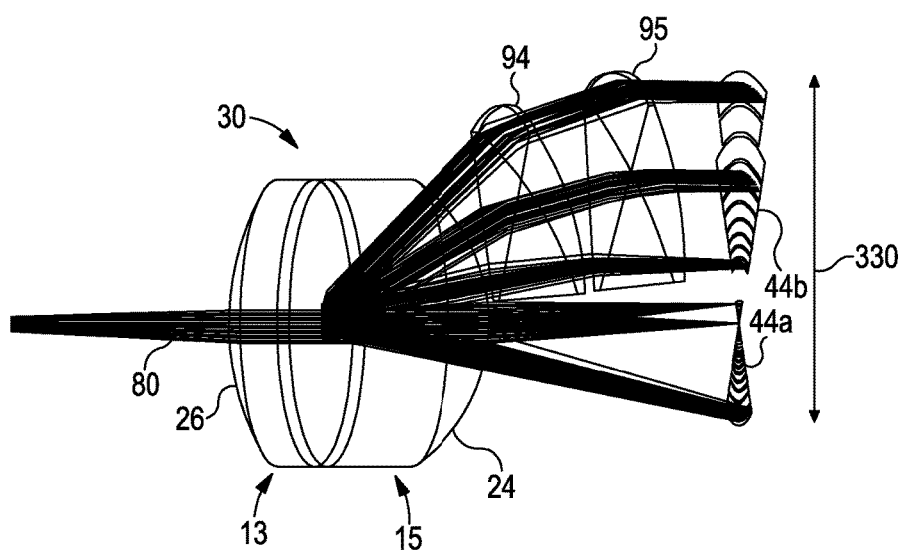
FIG. 33 is a ray diagram of a sample cell and a forward scatter detection arrangement according to an embodiment.

The embodiments of FIGS. 22 to 26 are relatively long, in order to achieve an appropriate level of performance. FIG. 33 shows an embodiment that addresses these shortcomings by providing a relatively compact configuration with good performance.

FIG. 33 shows a sample cell 30 and a forward scattering detection arrangement, comprising a first and second forward scattered light detector 44a and 44b.

The sample cell 30 in this embodiment is asymmetric, having a first cell wall 13 that is thinner than the second wall 15, and which has a convex surface 26 with larger radius of curvature than the covex surface 24 of the second cell wall 15. The internal walls of the sample cell 30 are again planar and parallel.

In order to push the focal point of the second cell wall 15 further from the cell, the second cell wall 15 has been made thicker without decreasing the radius of curvature of the convex surface 24, in effect adding a planar layer of glass to the lens, and increasing the total thickness of the lens so that it is no longer dominated by the chord height of the curved surface 24. In this embodiment, the chord height of the curved portion of the lens comprises less than half the total thickness of the wall 15. In some embodiments the proportion of the total thickness of the second wall 15 contributed by the chord height of the curved surface 24 may be no greater than 75%.

The first detector 44a is arranged for detecting light scattered at a first range of angles, comprising relatively low scattering angles. Light is collected and focussed at the first detector 44a by the second wall 15 of the sample cell 30. The first detector 44a extends to either side of the light beam axis, and the surface of the detector 44a is substantially normal to the light beam axis 8. The first detector 44a is arranged to detect light scattered at angles of 0.145° to 16.5°, The second detector 44b is arranged to detect light scattered at angles of 18.5° to 70°. Both the first and second detector 44a, 44b comprise focal plane arrays in the form of a one dimensional array of arc shaped detector elements.

A first and second lens 94, 95 are arranged to collect and focus scattered light at the second detector 44b. Each of the lenses 94, 95 comprise an aspheric surface. The lenses 94, 95 and second sample cell wall 15 are arranged to be parfocal, so that the first and second detectors 44a, 44b are at the same distance from the sample 22. In some embodiments, the first and second detector 44a, 44b may comprise a single focal plane array, or may comprise a plurality of detectors mounted on a common support substrate. The total combined height of the first and second detector 44a, 44b in this embodiment, indicated by 330, may be approximately 30 mm.

Figure 34:
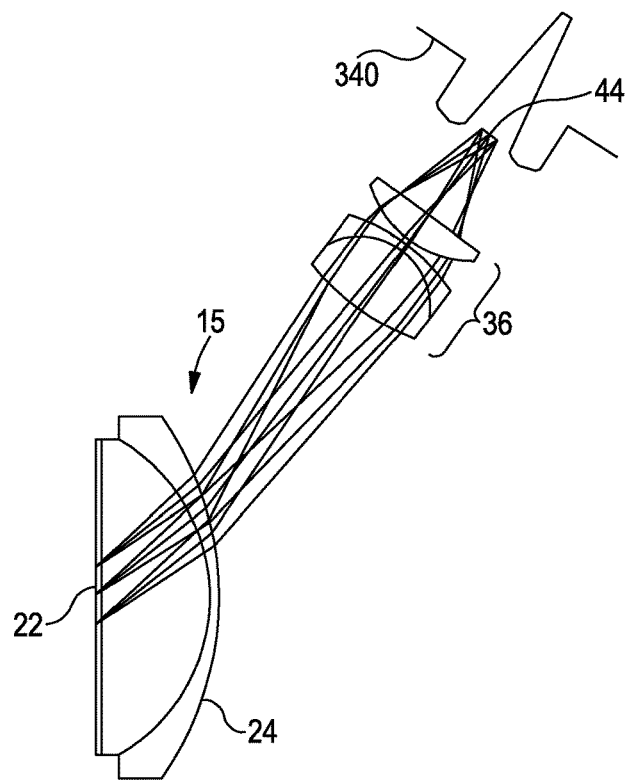
FIGS. 34 and 35 are comparative illustrations that respectively show the spatial distribution of scattered light according to different collection arrangements.
Figure 35:
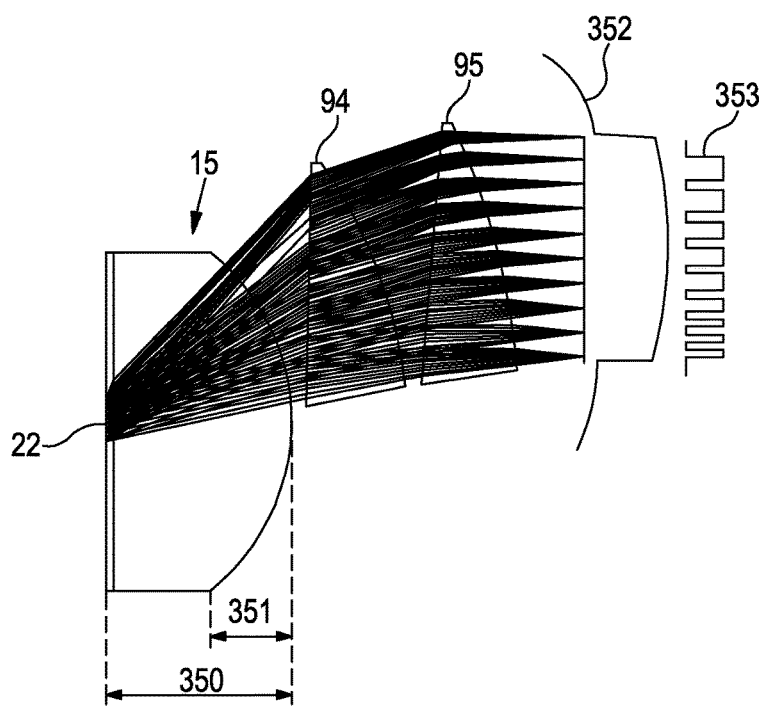

FIGS. 34 and 35 illustrate advantages that arise from the use of a detector arrangement for large angle scatter like that used in FIG. 33. Large angle scatter (scattering angles greater than 20 degrees, or 30 degrees, or 40 degrees) have previously been detected by angled discrete channel detectors. Arranging a single detector to receive a relatively large range of scattering angles by placing the detector normal to the light beam 8 and using a single collection optic (94, 95) to direct light scattered at a wide range of angles onto the detector, results in a substantially continuous light field 352 corresponding with a broad range of scattering angles at the detector. The sensitivity of the detector is represented by 353. A misalignment of the detector with the scattered light results in a shift in the mapping of scattering angle to detector, rather than the light "falling off" the edge of the detector. In contrast, for the conventional discrete high angle scattered light detector 44 shown in FIG. 34, a relatively small misalignment between the collection lens 36 and the detector may result in the shadow from the lens edges falling on the detector area, resulting in significant degradation of signal to noise ratio.

Figure 36:
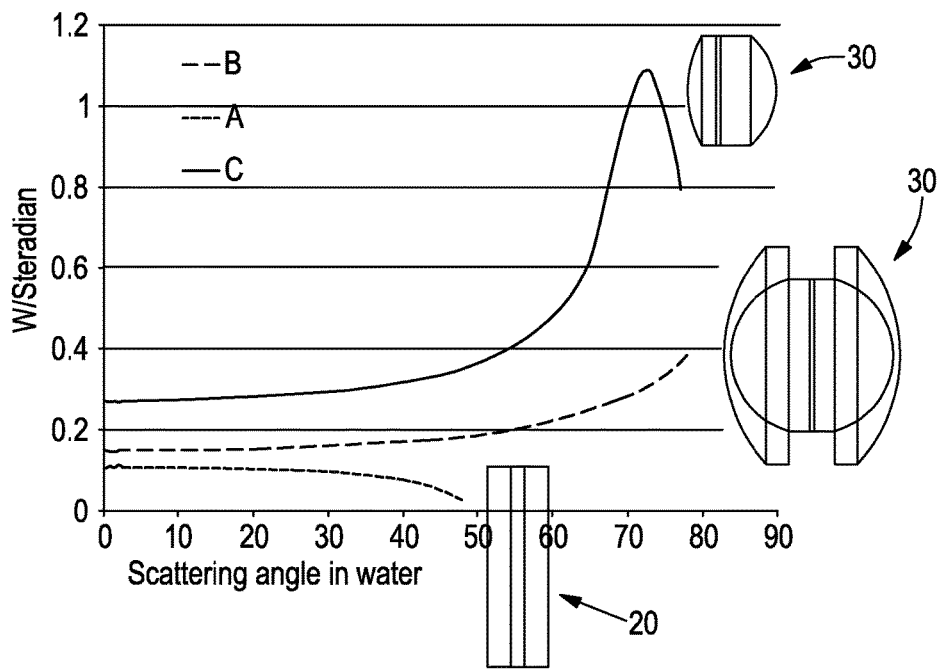
FIG. 36 is graph comparing the intensity of light per unit of solid angle for two embodiments, compared with a prior art arrangement.

FIG. 36 shows a comparison of the scattered light per steradian leaving the sample cell over a range of forward scattering angles for three different arrangements of sample cell. Curve A corresponds with a conventional prior art design of a flat windowed sample cell. Curve B corresponds with the symmetric doublet lensed sample cell arrangement shown in FIG. 4. Curve C corresponds with the asymmetric aspheric sample cell of FIG. 33. It is clear that much more light per solid angle is available for sample cell C, but sample cell B also results in large improvements over a flat walled sample cell. These differences are partly due to reduced reflections at the sample cell/air interface, but are also due to the refractive power of the lens reducing the divergence of scattered light as it exits the sample cell. Reducing the divergence of the scattered light results in increased power per unit area for detection.

Although the increased power for detection is advantageous, it is signal to noise ratio that is important for achieving high fidelity measurement, particularly in the context of detecting back scattered light. It is therefore instructive to consider stray light 371 in the back scatter direction that arises from the interaction of forward scattered light with the various lens elements and detectors of a forward scattering detection arrangement.

Figure 37:
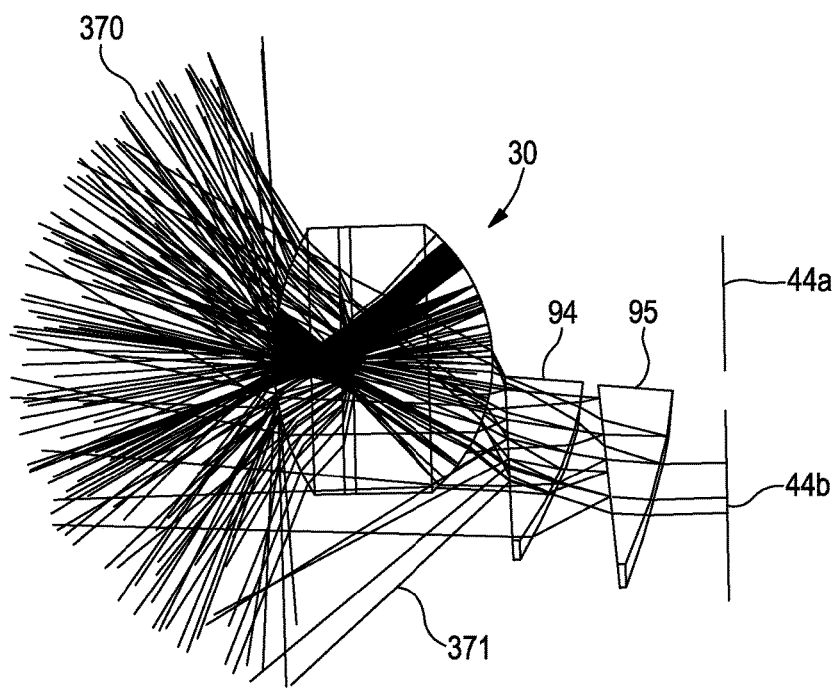
FIG. 37 is a ray diagram showing how stray light in the back scattering direction is simulated.

FIG. 37 illustrates a simulation of stray light in the back scattering direction resulting from forward scattered light. Reflections occur at interfaces of the sample cell 30, the lenses 94 and 95 and from the detectors 44a and 44b. The stray light in back scatter is measured at 370, over a 180° range of elevation and azimuthal angles.

Figure 38:
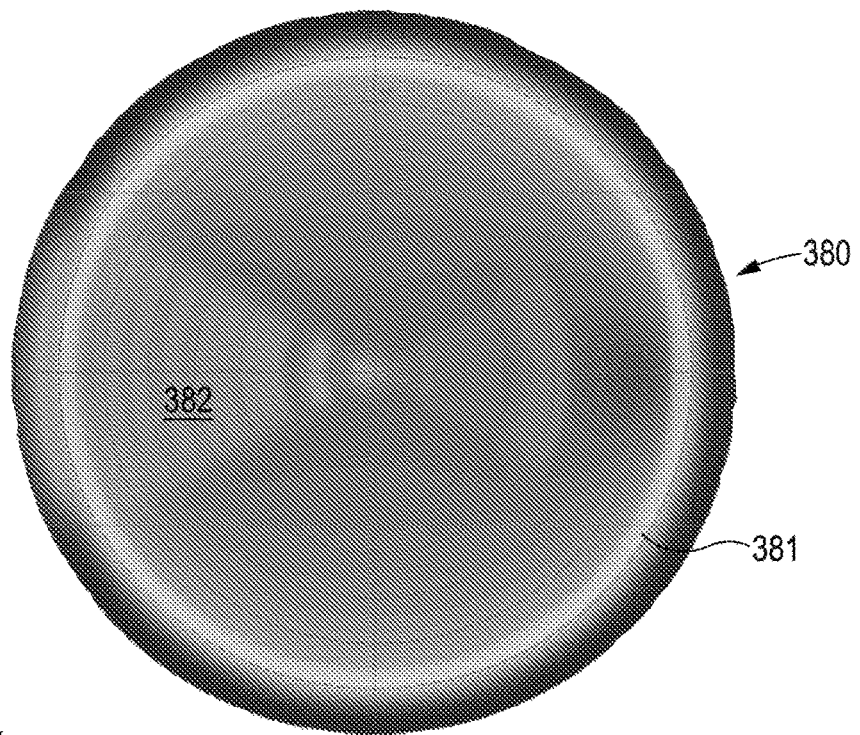
FIG. 38 is polar intensity plot of stray light in the back scattering direction for an embodiment, along with a two dimensional line graph of the intensity along a horizontal line through the centre of the polar intensity plot.
Figure 38:
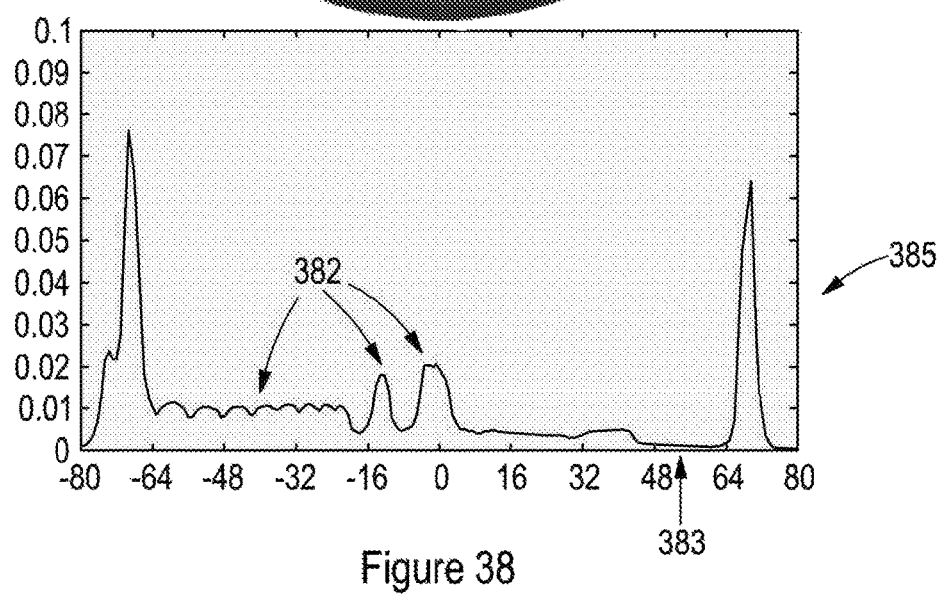

FIG. 38 shows the results on a polar intensity plot 380, in which the radial distance corresponds with elevation angle, the angle corresponds with azimuthal angle and the grayscale colour map corresponds with an intensity of light (with white being maximum intensity, and black being minimum intensity). For convenience we will define 0° azimuth as corresponding with a left pointing horizontal line on the plot 380, and clockwise angles as positive. A two-dimensional line plot 385 of the intensity with respect to elevation angle for 0° and 180° azimuth accompanies the intensity plot. A region of relatively high intensity 382 can be identified that results from reflections from the detectors 44a and 44b. A bright ring 381 can also be seen (with corresponding peaks 384 in the line plot), at around 70° back scattering angle. This is at least partly a result of large reflections at high angles of incidence at the sample/sample cell interface. The low reflectivity at 383 is due to the low reflections near the Brewster angle at the sample/sample cell interface.

Figure 39:
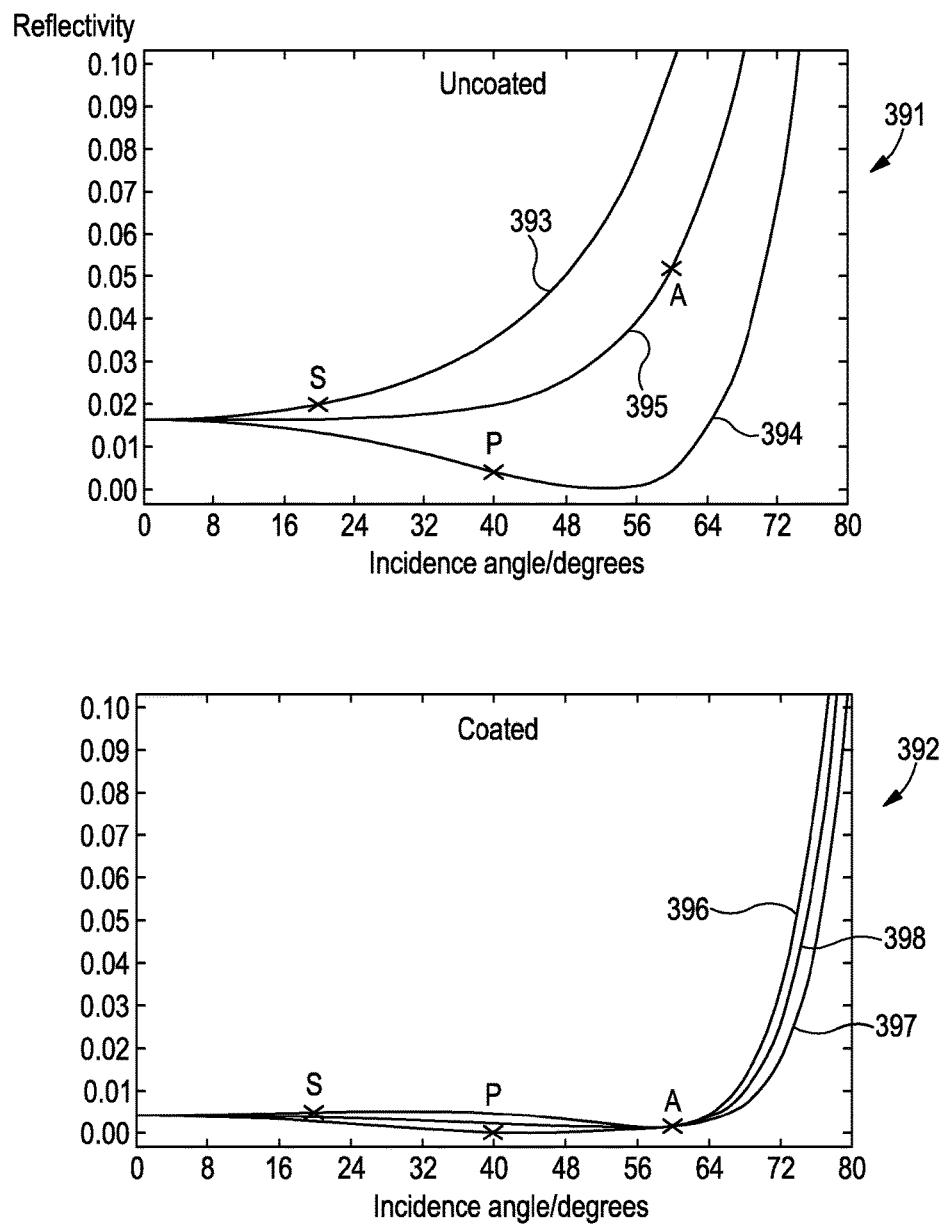
FIG. 39 is a pair of graphs showing reflectivity for the sample/sample cell interface (when the sample is water), the first graph corresponding to an uncoated sample/sample cell interface and the second graph corresponding to an anti-reflection (AR) coated sample/sample cell interface.

FIG. 39 includes a graph 391 of the reflectivity of this interface, for the case where the sample is water and the sample cell is glass, and where the surface is uncoated. Lines of reflectivity with respect to incidence angle are shown for S polarised light 393, P polarised light 394 and unpolarised light 395 (corresponding with the average of S and P). Graph 392 shows the similar graph, but for the case where the sample/sample cell interface is coated with an AR coating. Lines 396, 397 and 398 correspond with S, P and unpolarised light respectively. Clearly the AR coating substantially reduces reflections at this interface.

Figure 40:
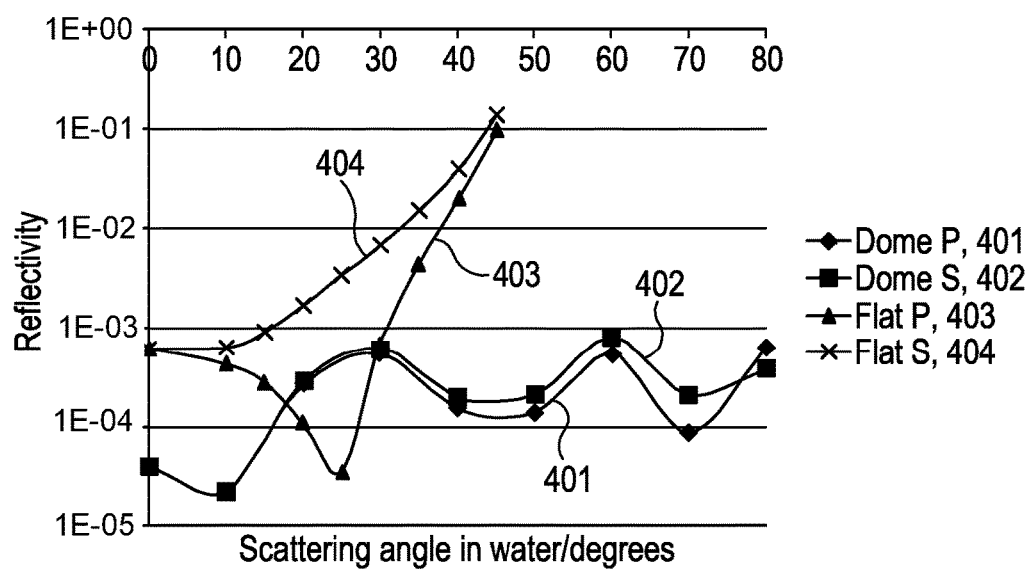
FIG. 40 is a graph showing reflectivity with respect to scattering angle at the sample cell/air interface for an AR coated sample cell according to an embodiment, and for AR coated sample cell with flat walls according to the prior art.

Further reflections from the sample cell 30 occur at the sample cell/air interface, at the convex surface 24. This surface has a relatively low radius of curvature, which means it is potentially challenging to achieve a uniform AR coating thickness. At the steeper portions of this surface, it is likely that the AR coating will be thinner than on the axis of the lens. The reflectivity of this interface with respect to the scattering angle in the sample 22 is shown in FIG. 40 assuming that the thickness of the AR coating varies according to a cosine of the surface normal. Results obtained for a prior art cell with flat windows having an AR coating are also shown in FIG. 40. Lines corresponding with S and polarised light 402, 401 for the lensed second cell wall 15 are shown, along with lines corresponding with S and P polarised light 404, 403 for the prior art sample cell with flat walls.

Due to the curvature of the interface 24, light scattered at relatively high angles has a relatively low angle of incidence at the interface (compared with the prior art flat walled sample cell). This results less difference in S and P polarised light reflectivity. Normally P polarised light is preferred for performing light scattering measurements due to reduced reflections at the scattering angles of interest, but the use of a lensed second cell wall 15 results in similar reflectivity for S and P polarised light over a broad range of forward scattering angles. S polarised light can therefore be collected in forward scatter, where the intensity of scattered light is higher. There has hitherto been a prejudice against detecting S polarised scattered light due to reflections in interfaces of the sample cell.

It is also clear from FIG. 40 that reflections are generally substantially lower for a sample cell having a second wall 15 that is a lens.

Figure 41:
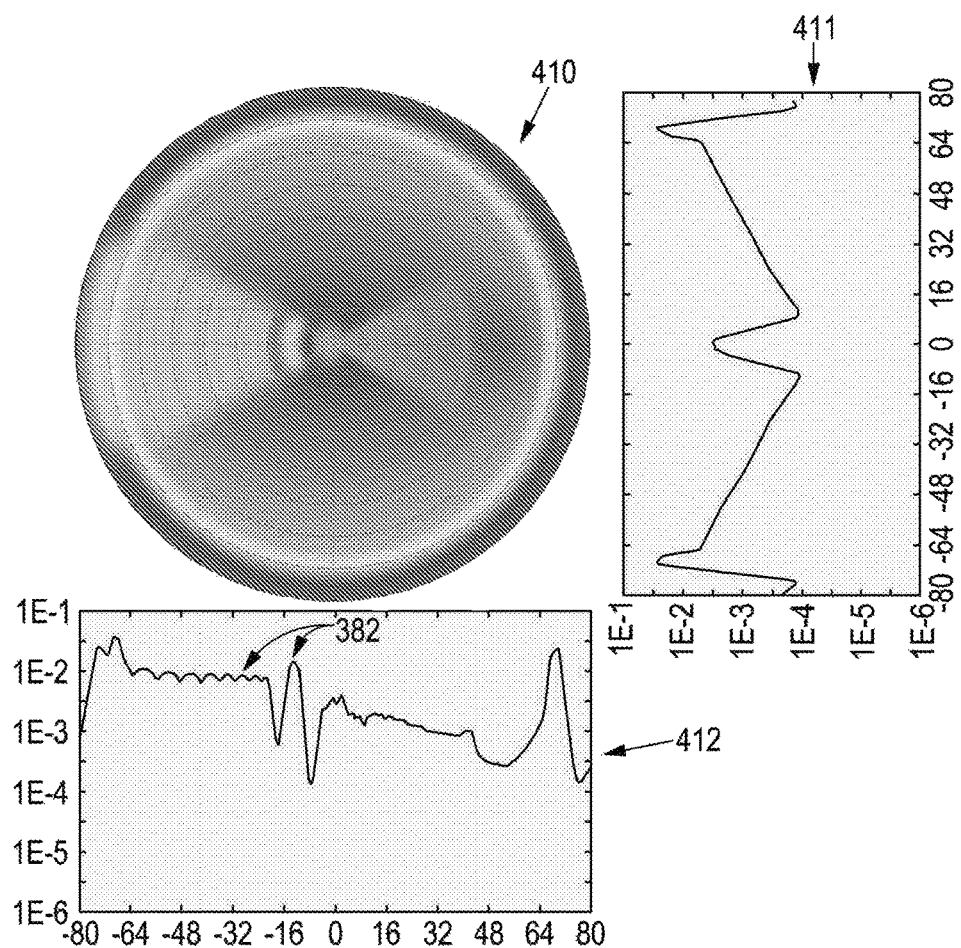
FIG. 41 is a polar intensity plot of stray light in the back scattering direction for an embodiment having AR coatings at the sample/sample cell interface and at the sample cell/air interface, along with two dimensional line graphs of the intensity along horizontal and vertical lines through the centre of the polar intensity plot.

FIG. 41 repeats the simulation that resulted in FIG. 38, but for a sample cell in which the sample/sample cell interface and the sample cell/air interface are both AR coated. FIG. 41 comprises a polar intensity plot 410, and line plots 411 and 412. Line plot 412 shows stray light intensity with respect to elevation angle, for an azimuthal angle of 0° and 180°, and line plot 412 shows stray light intensity with respect to elevation angle, for an azimuthal angle of 90° and 270°. Bright regions 382 resulting from reflections from the detectors 44a, 44b can clearly be seen. The bright ring 381 at around 70° has been substantially reduced in intensity by the AR coating at the sample/sample cell interface.

The effect of the AR coatings are to substantially reduce the stray light in the back scattering direction, to the point where reflections from the detectors 44a, 44b become a very significant stray light source. Regions 411 can be identified where stray light intensity is relatively low (below 0.001). These regions 411 are centred on 90° and 270° azimuth, in different azimuthal regions to the detectors 44a, 44b (which are respectively centred on 0° azimuth and 180° azimuth). The stray light in the back scatter direction for this embodiment is approximately 5 times lower than which results from a prior art design with flat cell walls, which will result in a factor of 5 improvement in signal to noise. In combination with the increased signal (as shown in FIG. 36), it is clear that very substantial improvements in signal to noise ratio are available in accordance with an embodiment.

A number of options are available for collecting and detecting the back scattered light leaving the sample cell (which we have established will have a very high signal to noise ratio). FIG. 42 shows an embodiment of a back scattering collection optic comprising a collector lens 99, condenser lens 100 and a detector 44e. This embodiment is a Köhler type optical arrangement, which may be configured to be insensitive to sample cell position by making it afocal. The detector 44e is a single pixel detector, and may have an area of 35 mm². The lenses 99, 100 and detector 44e may be arranged to be centred on a back scattering angle of 25° to detect back scattering angles of 8° to 42° where the sample is water (9.3° to 48° where the sample is air). The lenses 99, 100 and detector 44e are oriented at an angle to the incident light beam with this type of detector channel (not on the light beam axis). This approach is cost effective, and is shown in FIG. 43 in combination with the forward scatter arrangement already shown in FIG. 33.

An alternative to this single pixel detector approach is to use a similar detection arrangement for back scatter to that used for forward scatter. FIGS. 44 and 45 show an embodiment comprising a back scatter detection arrangement comprising two lenses 194, 195 and a focal plane array detector 42. The lenses 194, 195 and detector 42 are respectively the same as the lenses 94, 95 and detector 44b of the forward scatter detection arrangement described with reference to FIG. 33. This re-use of lenses and silicon increases the simplicity of the design and reduces costs. All of the collection lenses 94, 95, 194, 195 are aligned with their axis substantially co-incident with the light beam 8, and the plane of the detectors 44a, 44b, 42 are all substantially normal to the light beam 8, making the system very straightforward to assemble and align.

FIGS. 46 and 47 show an embodiment in which a discrete back scatter detection arrangement 99, 100, 42a (in which the collection optics 99, 100 and detector 42a are at an angle to the light beam 8) is combined with a focal plane array type back scatter detection arrangement 194, 195, 42 (in which the collection lenses 194, 195 and detector 42 are arranged on the illumination beam axis 8). The discrete back scatter detector arrangement 99, 100, 42a is that shown in FIGS. 42 and 43, and the focal plane array detector arrangement is that shown in FIGS. 44 and 45.

FIGS. 48 and 49 show graphs 480, 490 comparing the optical power at the detectors for a specific illuminating beam power, for embodiments (A), (B) and (C). In this graph: (A) corresponds with a prior art apparatus comprising discrete detectors for high angle scattering and a flat walled sample cell; (B) corresponds with the embodiment of FIG. 3, with discrete detectors each having their own angled collection lens; and (C) corresponds with the embodiment of FIGS. 46 and 47.

FIG. 48 is a linear graph 480, and FIG. 49 is a log/log graph 490. Each data point in (A), (B) and (C) corresponds to a detector (or detector element) location. Points 483 are detector locations on the focal plane array detectors 44a and 44b, points 482 are detector locations on the focal plane array detector 42, and point 481 is the detector 42a. It can be seen that the embodiment of FIGS. 46 and 47 is not configured to measure very small scattering angles (below 0.1 degrees), but provides substantially improved optical power at the silicon at almost every scattering angle, compared with either (A) or (B). Extending the range of the instrument to include lower scattering angles may be achieved at the expense of the size of the instrument by moving the small angle detector 44a further from the sample cell and using a diverging lens, like the approach of FIG. 24.

FIG. 50 compares the total collected light at the detectors for (A), (B) and (C), based on FIGS. 48 and 49. Embodiment (C) captures more than 20 times the total light at the detectors compared with the prior art, and more than twice that of (B). The total silicon detector area compares favourably with the prior art approach (A). Embodiment (C) uses a total silicon area of approximately 210 mm², and the prior art approach uses around 330 mm². The impact on signal to noise ratio of improvements in the total power of scattered light at the detectors is multiplicative with reductions in noise due to stray light at the detectors, so the total improvement in signal to noise ratio is likely to be of the order of at least 100 (compared with prior art arrangements).

As well as facilitating very large improvements in signal to noise by increasing signal and decreasing optical noise, a sample cell with lenses for walls also facilitates multi-modal analysis, because of the improved range of angles that light can enter and exit the cell (as already noted with reference to FIG. 19).

Discussion of the previous embodiments has focussed on a sample where the dispersant is water, but the invention is equally applicable to particulate samples dispersed in air. FIG. 53 shows an example embodiment in which the forward and back scatter detection arrangement remains the same as that shown in FIGS. 44 and 45, but in which the previous sample cell 30 (for samples in which the dispersant is water) has been replaced with a sample cell 31. A particle characterisation instrument may comprise both types of sample cell, and may be configured to switch which type of sample cell 30, 31 is positioned for illumination/detection.

The sample cell 31 for dry particulate dispersions comprises a first wall 13 and second wall 15 that are both plano-convex lenses, with the planar faces parallel and facing each other to define the interior of the sample cell 31. The walls 13, 15 are substantially symmetric about a central plane that is equidistant from the planar faces of the lenses, so that the sample cell approximates a Fourier lens system. The distance between the planar faces of the first and second wall 13, 15 is between 8 and 12 mm, preferably around 9.6 mm.

It will be appreciated that changing the sample cell from sample cell 30 to sample cell 31 results in different mapping of scattering angle to detector location, but this is straightforward to address by taking account of this in processing the detector output.

FIG. 54 shows a pair of embodiments 541, 542 in which the illuminating beam 8 is very narrow within the sample 22. This is achieved in embodiment 541 by positioning the light source 2 relatively close to the sample cell 30, and using a converging lens 6a positioned between the back scatter collection lenses 194, 195 and the sample cell 30 to produce a narrow beam waist near to the light source 2. In embodiment 542 the light source 2 is positioned further from the sample cell 30, and the converging lens 6a is on the opposite side of the back scatter collection lenses 194, 195 to the sample cell 30. A far beam waist is produced by this arrangement that is very narrow within the sample 22. The narrow beam width may facilitate scattering detection from a reduced number of particles or from single particles, which may enable improvements in relating the output of the detectors to the characteristics of the particles (e.g. size).

FIG. 55 is graph 550 showing the power (per unit of illuminating power) at the detectors of the embodiment of FIGS. 44 and 45 for a sample comprising protein particles or aggregates. The main peak 553 at a forward scattering angle of 1° can clearly be seen. The first minima 551 is at a scattering angle of between 2° and 3°. The higher order diffraction rings 552 are more visible for higher concentrations of particles. Curves 561, 562, 563, 564, 565, 566 are shown, respectively corresponding with concentrations of 0.5, 1, 2, 4, 8 and 16 particles per mm².

Example embodiments have been described in which a collecting lens with an aspheric surface is used to enable a more compact design. In these examples the detector with which the aspheric collecting lens is associated detects a relatively broad range of angles of scattered light, but this is not essential to the invention. It will be understood that a collecting lens with an aspheric surface enables a more compact optical design and this technical effect exists independently of whether the detector that is associated with the collecting lens is arranged to detect a broad range of scattering angles.

The skilled person will appreciate that a number of other modifications can be made, without departing from the scope of the invention, as defined by the appended claims.

The invention claimed is:

1. A particle characterization apparatus comprising:
a light source; a sample cell; a collecting lens comprising an open region; and a detector; wherein:
the light source is operable to illuminate a sample comprising dispersed particles within the sample cell with a light beam along a light beam axis, the light beam axis passing through a first wall of the sample cell, through the sample, and through a second wall of the sample cell, so as to produce scattered light by interactions with the sample;
the detector is configured to detect light scattered from the sample;
the second wall of the sample cell comprises a lens with a convex external surface through which the light beam axis passes; and
the collecting lens is arranged to collect and focus scattered light leaving the sample cell onto the detector and is arranged so that un-scattered light from the light beam passes through the open region without being reflected or refracted by the collecting lens, and comprises an aspheric surface.

2. The particle characterisation apparatus of claim 1, wherein the apparatus is configured such that the light beam axis does not pass through the aspheric surface.

3. The particle characterisation apparatus of claim 1, wherein the detector comprises a planar detector, and the aspheric surface of the collecting lens is configured to reduce field curvature at the planar detector.

4. The apparatus of claim 3, wherein the plane of the planar detector is substantially normal to the light beam axis.

5. The apparatus of claim 1, wherein the detector is arranged to detect light scattered from the sample at a range of angles to the light beam axis, the range of angles comprising a minimum scattering angle of 30 degrees or less, and a maximum scattering angle of 50 degrees or more.

6. The apparatus of claim 1, wherein the detector comprises an array of detector elements.

7. The apparatus of claim 1, wherein the collecting lens has an optical axis, and the collecting lens is arranged with its optical axis substantially coincident with the light beam axis.

8. The apparatus of claim 7, wherein the collecting lens is substantially sector shaped, when viewed along the optical axis of the lens.

9. The apparatus of claim 1, wherein the collecting lens is configured to focus light scattered from the sample on the detector with a point spread function that has a radial extent and a tangential extent, wherein the tangential extent is at least a factor of two greater than the radial extent.

10. The apparatus of claim 1, wherein the first wall of the sample cell comprises a lens with a convex external surface, and the first wall is arranged to collimate the light beam in the sample.

11. The apparatus of claim 1, wherein the second cell wall comprises a doublet lens.

12. The apparatus of claim 1, further comprising a processor configured to distinguish light scattered from bubbles in the sample from light scattered from particles in the sample based on the output of the detector.

13. The apparatus of claim 12, wherein the processor is configured to determine periods of time when the detector is detecting light that includes light scattered from a bubble in the sample.

14. The apparatus of claim 1, further comprising a second detector arranged to detect light scattered from the sample at angles of greater than 90 degrees to the light beam axis, wherein the second detector is substantially normal to the light beam axis.

15. The apparatus of claim 14, further comprising a second collecting lens, arranged to collect and focus light scattered from the sample at angles of greater than 90 degrees to the light beam axis onto the second detector, wherein the second lens has a lens axis, and the second lens is arranged with its lens axis substantially coincident with the light beam axis.

16. The apparatus of claim 1, comprising a detector element that is arranged to detect light scattered from the sample that passes through the second cell wall, but does not pass through the collecting lens, the detector element being substantially planar and substantially normal to the light beam axis.

17. The apparatus of claim 16, wherein the detector element is part of the detector.

18. The apparatus of claim 16, wherein the detector element is part of a further detector.

* * * * *